United States Patent
Ravenelle et al.

(10) Patent No.: US 10,561,735 B2
(45) Date of Patent: Feb. 18, 2020

(54) SOLID FORMULATIONS OF LIQUID BIOLOGICALLY ACTIVE AGENTS

(71) Applicants: Paladin Labs Inc., Montreal (CA); Paladin Labs Europe Limited, Dublin (IE); Paladin Labs (Barbados) Inc., Hastings, Christ Church (BB)

(72) Inventors: Francois Ravenelle, Montreal (CA); Sandra Gori, Montreal (CA); David Lessard, Montreal (CA); Laibin Luo, Pierrefonds (CA); Dorothee Le Garrec, Montreal (CA); Damon Smith, Saint-Laurent (CA)

(73) Assignees: Paladin Labs Inc., Montreal (CA); Paladin Labs Europe Limited, Dublin (IE); Paladin Labs (Barbados) Inc., Hastings (BB)

( * ) Notice: Subject to any disclaimer, the term of this patent is extended or adjusted under 35 U.S.C. 154(b) by 0 days.

(21) Appl. No.: 15/817,907

(22) Filed: Nov. 20, 2017

(65) Prior Publication Data
US 2018/0140706 A1 May 24, 2018

Related U.S. Application Data

(63) Continuation of application No. 14/844,493, filed on Sep. 3, 2015, now abandoned, which is a continuation (Continued)

(51) Int. Cl.
  *A61K 47/34* (2017.01)
  *A61K 9/00* (2006.01)
  (Continued)

(52) U.S. Cl.
  CPC ............ *A61K 47/34* (2013.01); *A61J 3/02* (2013.01); *A61K 9/0019* (2013.01);
  (Continued)

(58) Field of Classification Search
  None
  See application file for complete search history.

(56) References Cited

U.S. PATENT DOCUMENTS

| | | |
|---|---|---|
| 4,311,712 A | 1/1982 | Evans et al. |
| 4,370,349 A | 1/1983 | Evans et al. |

(Continued)

FOREIGN PATENT DOCUMENTS

| | | |
|---|---|---|
| CA | 2227284 A1 | 2/1997 |
| CA | 2548216 A1 | 6/2005 |

(Continued)

OTHER PUBLICATIONS

"Design and Evaluation of a Formulation for Oral Administration," Jiho, Inc., 1995, p. 247-248 with English translation of Items 1 and 4.

(Continued)

*Primary Examiner* — Carlos A Azpuru
*Assistant Examiner* — Casey S Hagopian
(74) *Attorney, Agent, or Firm* — Goodwin Procter LLP

(57) ABSTRACT

The instant invention relates to a solid product comprising a liquid biologically active agent which is intimately associated to a stabilizing agent; particularly a solid product that can be reconstituted to a clear, stable, stabilized nanodispersion or loaded micelles comprising a polymer as a stabilizing agent and a liquid, preferably water immiscible, biologically active agent. The instant invention is further directed toward a process for the production of the above solid product; particularly to micelles or nanodispersions produced by hydration of a cake or powder of the solid product, produced via an effective treatment of a stabilized solution comprising for example a polymer as a stabilizing agent, such as an amphiphilic block copolymer or a small molecular weight surfactant, loaded with a liquid biologi- (Continued)

cally active agent, such as propofol, an optional additive, and a suitable solvent.

19 Claims, 22 Drawing Sheets

Related U.S. Application Data of application No. 14/134,156, filed on Dec. 19, 2013, now abandoned, which is a continuation of application No. 11/286,301, filed on Nov. 25, 2005, now abandoned.

(60) Provisional application No. 60/631,755, filed on Nov. 29, 2004.

(51) Int. Cl.
| | | |
|---|---|---|
| *A61K 9/107* | (2006.01) | |
| *A61K 9/19* | (2006.01) | |
| *A61K 31/08* | (2006.01) | |
| *A61K 31/47* | (2006.01) | |
| *A61K 47/32* | (2006.01) | |
| *A61K 31/05* | (2006.01) | |
| *A61J 3/02* | (2006.01) | |
| *A61K 31/085* | (2006.01) | |
| *B01F 3/08* | (2006.01) | |

(52) U.S. Cl.
CPC .......... *A61K 9/0095* (2013.01); *A61K 9/1075* (2013.01); *A61K 9/19* (2013.01); *A61K 31/05* (2013.01); *A61K 31/08* (2013.01); *A61K 31/085* (2013.01); *A61K 31/47* (2013.01); *A61K 47/32* (2013.01); *B01F 3/088* (2013.01); *B01F 2003/0884* (2013.01)

(56) References Cited

U.S. PATENT DOCUMENTS

| | | | |
|---|---|---|---|
| 4,997,454 A | | 3/1991 | Violante et al. |
| 5,543,158 A | | 8/1996 | Gref et al. |
| 5,683,723 A | | 11/1997 | Spenlehauer et al. |
| 6,306,433 B1 | | 10/2001 | Andersson et al. |
| 6,322,805 B1 | | 11/2001 | Kim et al. |
| 6,338,859 B1 | * | 1/2002 | Leroux ............... A61K 9/1075 424/426 |
| 6,780,324 B2 | | 8/2004 | Le Garrec et al. |
| 6,780,428 B2 | | 8/2004 | Ranger et al. |
| 6,835,396 B2 | | 12/2004 | Brynjelsen et al. |
| 6,939,564 B2 | | 9/2005 | Ranger et al. |
| 7,018,655 B2 | | 3/2006 | Lele et al. |
| 7,034,013 B2 | | 4/2006 | Thompson et al. |
| 7,094,810 B2 | | 8/2006 | Sant et al. |
| 7,262,253 B2 | | 8/2007 | Luo et al. |
| 7,510,731 B2 | | 3/2009 | Ranger et al. |
| 7,838,600 B2 | | 11/2010 | Luo et al. |
| 2002/0106390 A1 | | 8/2002 | Huglin et al. |
| 2002/0120015 A1 | | 8/2002 | Dennis et al. |
| 2003/0138489 A1 | * | 7/2003 | Meadows ............ A61K 9/0019 424/486 |
| 2003/0175313 A1 | * | 9/2003 | Garrec ................ A61K 9/1075 424/400 |
| 2003/0190347 A1 | * | 10/2003 | Supersaxo ........... A61K 9/1075 424/450 |
| 2006/0198891 A1 | | 9/2006 | Ravenelle et al. |
| 2009/0258071 A1 | | 10/2009 | Lessard et al. |
| 2012/0289606 A1 | | 11/2012 | Ravenelle et al. |
| 2013/0039864 A1 | | 2/2013 | Ravenelle et al. |
| 2014/0323587 A1 | | 10/2014 | Ravenelle et al. |

FOREIGN PATENT DOCUMENTS

| | | |
|---|---|---|
| CA | 2589242 A1 | 6/2006 |
| CA | 2700426 A1 | 4/2009 |
| CN | 1416902 | 5/2003 |
| EP | 0520888 A1 | 12/1992 |
| JP | 2008-521775 A | 6/2008 |
| WO | WO-1997/10814 A1 | 3/1997 |
| WO | WO-1998/14174 A1 | 4/1998 |
| WO | WO-1999/13914 A1 | 3/1999 |
| WO | WO-2001/64187 A2 | 9/2001 |
| WO | WO-2002/00194 A2 | 1/2002 |
| WO | WO-2002/45709 A1 | 6/2002 |
| WO | WO-2002/074200 B1 | 3/2003 |
| WO | WO-2003/030802 A2 | 4/2003 |
| WO | WO-2003/030862 A2 | 4/2003 |
| WO | WO-2003/063824 A2 | 8/2003 |
| WO | WO-2003/077882 A2 | 9/2003 |
| WO | WO-2005/058250 | 6/2005 |
| WO | WO-2006/056064 | 6/2006 |
| WO | WO-2007/073596 A1 | 7/2007 |
| WO | WO-2008/035229 | 3/2008 |
| WO | WO-2009/040818 | 4/2009 |

OTHER PUBLICATIONS

English Translation of Office Action for Japanese Application No. JP 2007-541612, 3 pages.
English Translation of Office Action for Japanese Application No. JP 2013-505286, 5 pages.
Examination Report for European Patent Application No. 05815074, dated Apr. 4, 2014 (4 pages).
Extended European Search Report dated Aug. 16, 2012 for Application No. 05815074.9 completed on Aug. 8, 2012 (6 pages).
Package insert for Diprivan® 1% Injectable Emulsion (4 pages).
English Translation of Office Action for Japanese Application No. JP2017-094186, dated Dec. 4, 2018, 3 pages.

\* cited by examiner

SOLID FORMULATIONS OF LIQUID BIOLOGICALLY ACTIVE AGENTS

CROSS-REFERENCE TO RELATED APPLICATIONS

This application is a continuation of U.S. patent application Ser. No. 14/844,493, filed Sep. 3, 2015, which is a continuation of U.S. patent application Ser. No. 14/134,156, filed Dec. 19, 2013, which is a continuation of U.S. patent application Ser. No. 11/286,301, filed Nov. 25, 2005, which claims priority to and the benefit of U.S. Provisional Patent Application No. 60/631,755, filed Nov. 29, 2004, the entire disclosures of each of which are incorporated by reference herein in their entireties.

BACKGROUND OF THE INVENTION a) Field of the Invention

This invention relates to the preparation of a solid product in the form of a cake, a powder, or the like, by mixing a solvent comprising water, an aqueous solution, at least one non-aqueous organic solvent, or combinations thereof, with at least one stabilizing agent, and subsequently adding at least one liquid biologically active agent to the above mixture; and treating the whole under conditions to give the above solid product which is substantially solvent free. More particularly, the invention relates to the above solid product and a method for rapid reconstitution thereof in an aqueous media, whereby an essentially clear, lipid free, sterile, stable aqueous product is formed containing nanodispersions or micelles of the aforementioned stabilizing and biologically active agents; and to a method of treating a patient in need of said biologically active agent by administration of said stable aqueous product thereto. In a preferred embodiment, the biologically active agent is water immiscible and may be selected from 2,6-bis-(1-methylethyl)phenol or 2,6-diisopropylphenol commonly known as propofol, 2-phenoxyethanol, quinaldine, methoxyflurane and the like and combinations thereof. The most preferred biologically active agent is propofol.

b) Description of the Prior Art

Propofol (known as 2,6-bis-(1-methylethyl)phenol, also known as 2,6-diisopropylphenol) is currently the most popular anaesthetic in the world. It is used for the induction and maintenance of anaesthesia or sedation upon administrations to humans or animals, Intravenous injection of a therapeutic dose of propofol produces hypnosis rapidly and with minimal excitation, usually within 40 seconds from the start of an administration. Fast onset and short half life (10-15 minutes) allows for a clinically useful profile with prompt recovery. Due to the rising cost of health care, this quick recovery time is especially advantageous for increasingly common outpatient procedures.

At room temperature, propofol is an oil that is immiscible with water (aqueous solubility of approximately, 0.154 mg/mL) and is supplied in a emulsion, at concentrations of 1% or 2% (w/w) (2% is used for longer sedation). Propofol oil-in-water emulsions currently on the market are DIPRIVAN® (manufactured by AstraZeneca Pharmaceuticals, Inc.), BAXTER® IPP (manufactured by Gensia Sicor, Inc), and Propofol injectable emulsion (Manuf. Bedford Laboratories).

Extreme care must be taken during manufacture to thoroughly distribute the propofol in the emulsion, as large droplet sizes of propofol in the blood stream have been linked to embolism in humans. These emulsions typically contain: soybean oil (100 mg/mL), glycerol (22.5 mg/mL) and egg lecithin (12 mg/mL). Emulsions are defined by a large particle size, generally of more than 200 nm, thereby creating a milky white opaque formulation. This causes visual inspection for foreign particles in the formulation by the anesthesiologist, to be more difficult. The high lipid content of these emulsions has been linked to hyperlipidaemia.

The presence of the egg lecithin and soybean oil in these emulsions also makes them highly susceptible to microorganism growth and allergic reactions. In order to suppress bacterial growth, manufacturers have added the preservative EDTA (ethylene diamine tetraacetic acid) at 0.05 mg/mL to DIPRIVAN® and sodium metabisulfite at 0.25 mg/mL, to BAXTER® PPI propofol, and benzyl alcohol at 1 mg/ml to propofol injectable emulsion of Bedford Laboratories.

Some of these preservatives have been known to cause adverse reactions in humans. Sodium metabisulfite is a sulfite known to cause allergic-type reactions including anaphylactic symptoms and life-threatening or asthmatic episodes in certain sulfite sensitive individuals. Sodium bisulfite has also been shown to catalyze propofol degradation. Similarly, the chelating properties of EDTA are of concern to the FDA due to their unfavorable effects on cardiac and renal function. Moreover, these emulsions cannot be effectively sterilized using standard sterilizing filters, as they are too thermodynamically unstable and tend to separate under the shear force required. Such emulsions are also unstable versus dilution and/or mixing with saline, dextrose or other medication containing solutions. Furthermore, the presence of egg lecithin as an emulsifier and soybean oil as a solubilizer may produce anaphylactic and anaphylactoid reactions in persons allergic to eggs and/or soybeans.

Propofol emulsions are known to be thermodynamically unstable, that is, the oil and water components have a tendency to separate when diluted, sheared, cooled, heated, or mixed with other solutions. Furthermore, this separation is accelerated when the formulation is stored at low temperatures, i.e. below 2° C., or at elevated temperatures, i.e. above 25° C. In addition, these lipid-based emulsions have been associated with pain at the injection site, often causing the concomitant use of a topical anaesthetic upon injection.

A variety of methods and procedures have been described in the prior art for preparing stable formulations for the effective delivery of at least one hydrophobic compound, particularly pharmaceutical drugs, to a desired location in the body. A number of these methods are based on the use of auxiliary solvents; surfactants; soluble forms of the drug, e.g., salts and solvates; chemically modified forms of the drug, e.g., prodrugs; soluble polymer-drug complexes; special drug carriers such as liposomes; and others.

Indeed, the use of surfactant based micelles has attracted a great deal of interest as a potentially effective drug carrier that is capable of solubilizing a hydrophobic drug in an aqueous environment. Typically, micelles and nanodispersions have been shown to alter the pharmacokinetics (and usually the pharmacodynamics) of the biological agent to be delivered. Thus, by sequestering the drug within them, they may prolong the circulation time, may allow more drug to be delivered to a specific location, and/or may allow a different biodistribution when compared to administration of the drug alone.

However, each of the above procedures is associated with certain drawbacks, especially when considering the delivery of "on/off" type anaesthetics, such as propofol. For example, the method based on the use of surfactant micelles to solubilize hydrophobic drugs can be inherently problematic in that some of the surfactants are relatively toxic (e.g. Cremophor EL®) and that precipitation of hydrophobic drugs may occur when subjected to dilution. Other methods of preparation yield poor entrapment efficiencies (e.g. equilibration methods), relatively large particle sizes (emulsions), or are time-consuming.

Finally, the prolonged circulation time associated with micellar or liposomal delivery can detrimentally affect the "on/off" properties required of an anaesthetic drug such as propofol Likewise, there have been studies based on the use of cyclodextrin derivates, which are water-soluble cyclic carbohydrate compounds with hydrophobic interior cavities that complex with propofol allowing dissolution of the drug in water to form a clear solution. However, cyclodextrins are expensive and have been associated with hemodynamic adverse events. Also, long-term stability of cyclodextrin formulations has been an issue with formulators. More importantly, cyclodextrins have been linked with renal toxicity at high doses.

There have also been various attempts investigating the use of water-soluble prodrugs comprising a propofol phosphate. However, usually prodrugs require much higher doses (up to ten times and more) for the same response as the instant invention and usually demonstrate a slower onset of action and slower clearance. Moreover, in some propofol prodrugs one of the bi-products is formaldehyde, a probable carcinogen. Prodrugs are also notably unstable resulting in short shelf lives or low storage temperatures to maintain their stability. The beneficial pharmacokinetics are changed due to the use of prodrugs.

Furthermore, when a liquid biologically active agent such as propofol is formulated with the technologies discussed above, a liquid dosage form is produced. However, the stability of such liquid formulations is always a concern with respect to duration and storage conditions.

Thus, what is lacking in the art is a light-weight, dry powder or cake formed from a water immiscible liquid drug, such as propofol, that is stable in several different temperature and dilution conditions for prolonged periods, that is readily reconstituted using aqueous media to produce essentially clear, sterile liquids which do not support bacterial growth, comprising drug-loaded micelles or nanodispersions in an aqueous medium. The micelles or nanodispersions, which are produced directly and spontaneously after addition of the aqueous reconstitution medium, allows high loading levels of propofol or other biologically active liquids to be achieved with substantially no effect on stability.

Many studies, literature articles and patents have been directed toward forming stable anaesthetic compositions suitable for parenteral administration, particularly the administration of propofol and other drugs in liquid form.

For example, WO 02/45709 A1 discloses a stable, clear and sterile aqueous composition comprising propofol, a water-soluble emulsifier (TPGS) and water, suitable for parenteral administration and a process for making the same. However, the final product is a liquid and the process of manufacturing requires both the filtration of the composition through a micron-sized filter and autoclaving the sealed container filled with the filtrate in order to achieve effective sterilization.

WO 03/030862 A2, discloses inhalation anaesthetic compositions and methods comprising a suspension of the anaesthetic in an aqueous solution. The reference teaches the use of surfactant poloxamers, (known as Pluronics® in the United States and Lutrols® in Europe) to encapsulate the anaesthetic (i.e. propofol) within the micelles. The preferred embodiments require the presence of propylene glycol in order to achieve adequate solubilization of propofol. However, the product is supplied as a liquid and the presence of water in the inhaled anaesthetic is not always beneficial to patients with pulmonary disorders, such as plural effusion. It will be noted that the composition disclosed in this reference is prepared using a mixture of liquids to constitute a liquid composition.

WO 01/64187 A2 and corresponding U.S. PGPUB No. 2003/0138489 A1, on the other hand, disclose propofol solubilized in aqueous micellar preparations using combinations of poloxamers to form a clear, injectable solution without inclusion of water-miscible co-solvents, such as propylene glycol. According to WO 01/64187 A2, the use of water-miscible co-solvents can have undesirable medical effects, such as superficial thrombophlebitis, intravasal, haemolytic reactions, and possible increase in formation of free propofol. Moreover, WO 01/64187 A2 indicates that autoclaving may be undesirable when the formulation is filtered to sterility since autoclaving has been known to disrupt the micelles, to the extent of requiring re-emulsification. In addition, poloxamers are detergent-like surfactants that are not readily degradable and may open-up tight junctions. Moreover, detergent surfactants may be a source of pain upon injection and require the addition of lidocaine to reduce local pain. The final product is a liquid.

U.S. Pat. No. 6,322,805 discloses a biodegradable polymeric drug carrier micelle composition capable of solubilizing a solid hydrophobic drug in a hydrophilic environment. The patent discloses a biodegradable polymeric drug carrier micelle and a hydrophobic drug wherein the drug is physically trapped within and not covalently bonded to the polymeric drug carrier micelle. The drug carrying micelle is capable of dissolving in water to form a solution thereof, and the drug carrier comprises an amphiphilic block copolymer having a hydrophilic poly(alkylene oxide) component, and a biodegradable hydrophobic polymer component selected from the group consisting of poly(lactic acid), poly(glycolic acid), poly(lactic-co-glycolic acid), poly(ε-caprolactone), a derivative thereof or a mixture thereof. The disclosed micelle is characterized as a solubilizing agent for a hydrophobic drug. The hydrophobic drug is mixed with the polymeric drug carrier micellar solution and the mixture is either stirred, heated, subjected to ultrasonic treatment, solvent evaporation or dialysis so as to incorporate it into the hydrophobic polymer core, after which it is formed into an aqueous solution.

U.S. Pat. No. 5,543,158 discloses nanoparticles or microparticles formed of a block copolymer consisting essentially of poly(alkylene glycol) and a biodegradable polymer, poly(lactic acid). In the nanoparticle or microparticle, the biodegradable moieties of the copolymer are in the core of the nanoparticle or microparticle and the poly (alkylene glycol) moieties are on the surface of the nanoparticle or microparticle in an amount effective to decrease uptake of the nanoparticle or microparticle by the reticuloendothelial system. Thus, the nanoparticles or microparticles are designed to circulate for prolonged periods within the blood fluids. In this patent, the molecular weight of the block copolymer is too high to be soluble in water, and a nanoparticle can only be prepared by first dissolving the block copolymer and a drug in an organic solvent, forming an o/w emulsion by sonication or stirring, and then collecting the precipitated nanoparticles containing the drug. The patent fails to provide the concept of solubilization of hydrophobic drugs, nor does it teach or suggest the formation of a clear, sterilizable solution containing the polymer/drug blend and subsequent lyophilization thereof, resulting in a readily dispersible micelle or nanodispersion, formed upon reconstitution.

EP 0520888 A1 discloses nanoparticles made of a poly(lactic acid) and poly(alkylene oxide) block copolymer. A high molecular weight poly(lactic acid) is used and a surfactant is employed in preparing a colloidal suspension of the nanoparticles. In this patent, nanoparticles are prepared by dissolving the block copolymer and a drug in an organic solvent, emulsifying the organic solution in water, and evaporating the organic solvent to precipitate the nanoparticles containing the drug. The resulting nanoparticles are fine particles having both hydrophilic and hydrophobic components and they cannot form clear stable aqueous liquids.

U.S. Pat. No. 4,997,454 teaches a method for making uniformly sized particles from solid compounds for intravenous administration as suspensions of particles of three microns in diameter, or less. A suitable solid compound is dissolved in a suitable solvent, and a precipitating liquid is infused to form non-aggregated particles which are separated from the liquid mixture. The product is a liquid comprising a suspension of solid microspheres.

U.S. Pat. Nos. 4,370,349 and 4,311,712 disclose a process for preparing a freeze-dried, liposomal, mixture which comprises either (a) dissolving at least one liposome-forming amphiphilic lipid, at least one biologically-active compound, and optionally one or more adjuvants, in a suitable solvent, and then freeze-drying the solution, or (b) preparing by any known method an aqueous liposome composition containing at least one biologically-active compound, and then freeze-drying the said aqueous liposome composition. The patents are particularly directed toward a process for preparing an aqueous liposome composition which comprises dispersing said freeze-dried, potential liposomal, mixture, obtained by procedure (a) or (b), in a suitable aqueous medium. The process of the instant invention is not directed toward liposome production.

U.S. Pat. No. 6,780,324 teaches a unique process wherein a solution is formed from a hydrophobic biologically active agent, in combination with a dispersing agent and a suitable solvent or solvent blend (which may further include water), the mixture being lyophilized and thereafter rehydrated to form a biologically active agent loaded micelle or nanodispersion. The instant invention provides an improved method for forming a biologically active agent loaded micelle or nanodispersion from a liquid hydrophobic biologically active agent by first forming a solution of a stabilizing agent and solvent (which solvent may solely comprise water), to which is added a liquid hydrophobic biologically active agent. This is followed by lyophilization and/or any treatment that will result in a solid product that is substantially free of solvent.

U.S. Pat. No. 6,835,396 discloses the preparation of submicron sized particles by mixing a pharmacologically active compound with a water immiscible solvent to form an organic phase. On the other hand there is provided an aqueous phase containing a surface active compound. The organic phase and the aqueous phase are combined to form a crude dispersion and the latter is treated with a sonication device allowing cavitation to occur. The dispersion is then frozen and lyophilized to provide particles having a mean particle size of less than 500 nm.

Ideally therefore, propofol should be available as a solid product that can instantaneously be hydrated to form a clear stable solution ready for injection. For this purpose, a test was made by lyophilizing a mixture of water and propofol. The result is that water and propofol had all evaporated and nothing remained. This is an indication that other avenues must be investigated.

Accordingly, it is a main objective of the instant invention to provide a process for the formation of a sterile, solid loaded micelle or nanodispersion comprising a liquid biologically active agent in an amphiphilic biodegradable polymer.

An additional objective of the invention is to produce a stable cake or powder that is readily reconstituted to form an essentially clear aqueous liquid containing a stabilized drug nanodispersion or loaded micelle.

It is still a further objective of the instant invention to provide a process whereby a clear liquid comprising a biologically active agent, polymer and optionally an additive (e.g. a bulk forming agent, a cryoprotectant, a lyoprotectant) and/or stabilizer is formed using any suitable solvent prior to a treatment such as freeze-drying, spray drying, and the like.

Another objective of the present invention is to provide a storable powder that is instantaneously reconstituted before administration to a patient for long-term infusions as well as bolus (highly concentrated) injections.

Another objective of the present invention is to provide micelles or nanodispersions loaded with liquid biologically active agents that release quickly into body fluids and tissues post administration.

Yet another objective of the instant invention is the formation of a powder that yields a longer shelf life and lighter product.

It is still a further objective of the invention to provide a sterile formulation without the need for preservatives.

Another objective of the invention is to provide a formulation that reduces or eliminates any sensation of pain upon administration commonly, which has been associated with currently marketed formulations.

It is a further objective of the instant invention to provide, once reconstituted, a liquid medical formulation that is stable for more than 24 hours at high drug loading levels at room temperatures.

Another objective of the present invention is to provide a formulation that is stable after dilution, when subjected to shear forces, or when mixed with saline, dextrose or other medication containing solutions (e.g. injectable lidocaine solutions).

Another objective of the present invention is to provide a solid formulation that, upon reconstitution, does not support bacterial growth.

Another objective of the present invention is to provide a formulation that is lipid free.

Definitions

The term "stabilizing agent" as used in the present specification and claims, is intended to mean a vehicle or material which allows aqueous preparations of water insoluble drugs.

The term "essentially clear" as used in the present specification and claims, is intended to mean a stable solution of a reconstitution solvent and a reconstituted solid, wherein a solid product comprising an intimate mixture of at least one stabilizing agent and at least one liquid biologically active agent loaded within the stabilizing agent, upon reconstitution, forms a clear stable reconstituted solution in which said at least one biologically active agent is present as stabilized nanodispersions or loaded micelles up to about 13% drug loading level, an increasingly opalescent solution at about 13% to about 20% drug loading level, and a transparent, cloudy suspension at greater than about 20% drug loading level. Nevertheless, all of these formulations of the instant invention are stable for more than 24 hours, i.e. they do not precipitate upon dilution in water and/or albumin 35 g/L solution. PPF-PM means propofol-polymeric micelle

SUMMARY OF THE INVENTION

In order to overcome the problems encountered by the prior art, the instantly disclosed invention relies on a treatment, such as lyophilization, spray drying, or the like well known to those skilled in the art, which is obtained by mixing a solvent selected from water, an aqueous solution, at least one non-aqueous organic solvent, or combinations thereof with at least one stabilizing agent under conditions to provide a first solution, to which is subsequently added at least one liquid biologically active agent such as propofol or the like, to give a second solution. The latter is lyophilized, spray-dried, or the like under conditions which yield a solid product, in which the liquid biologically active agent is intimately associated, and from which substantially all the solvent or solvents have been removed and where virtually no loss of drug occurs during the treatment; optionally an additive, non-limiting examples of which include a buffer, a bulk forming additive, a cryoprotectant, and a lyoprotectant may be added at any stage during the treatment.

Such a liquid can be subjected to a sterilizing filtration step prior to the above treatment to form a powder, a cake or the like. The solid product resulting from the above treatment is a light-weight, lipid free material that can be stored, transported and then reconstituted prior to use by the addition of an aqueous solution e.g. water, saline, dextrose or the like to form essentially clear, stable, sterile, liquids comprising nanodispersions or micelles in aqueous medium.

The instant process illustrates a simple and elegant procedure for forming a solid product from a liquid containing an intimate association of an insoluble liquid drug and a stabilizing agent. The liquid, comprising an intimate association of the solvent, insoluble liquid drug and stabilizing agent, may be dried by a process, whereby the insoluble liquid drug remains in close association with the stabilizing agent such that virtually all drug is retained during the process. The product is a dry, solid as mentioned above. The dry solid product upon addition of water or an aqueous solution spontaneously reconstitutes to form an essentially clear stable liquid comprising drug micelle or drug nanodispersions loaded with a liquid biologically active agent.

Broadly, the invention relates to a solid product suitable for reconstitution to a clear, stable solution upon addition of an aqueous solvent thereto, the solid product comprising an intimate mixture of at least one stabilizing agent, and at least one liquid biologically active agent, non-limiting examples of which are propofol, 2-phenoxyethanol, quinaldine, methoxyflurane, and the like, loaded within the stabilizing agent, in such a manner that the liquid biologically active agent is intimately associated with the stabilizing agent in a substantially solid product. The substantially solid product upon rehydration with a reconstituting aqueous solvent or solution, is capable of forming the essentially clear stable solution in which at least one biologically active agent is present as nanodispersions or micelles loaded with the at least one biologically active agent.

The invention also relates to a process for the production of a solid product suitable for reconstitution to a clear stable solution upon addition of an aqueous solution thereto, which is produced by forming a first mixture comprising a solution of at least one stabilizing agent, and at least one solvent, under conditions to achieve micelle or nanodispersion formation, subsequently adding at least one liquid biologically active agent, such as propofol, 2-phenoxyethanol, quinaldine, methoxyflurane, and the like, to the first mixture in such a manner to load the micelle or nanodispersion therewith and form a second mixture, and treating the second mixture under conditions effective to remove the solvent therefrom while forming a substantially solid product that contains the liquid biologically active agent intimately associated with the stabilizing agent, the solid product upon rehydration being capable of forming an essentially clear stable solution in which the at least one biologically active agent is present as a nonodispersion or micelle loaded with the at least one biologically active agent.

The invention also comprises a process for the production of a stabilized nanodispersion or loaded micelle containing a liquid biologically active agent by hydrating the above solid product under conditions to provide a stabilized nanodispersion or loaded micelle containing the liquid biologically active agent.

The invention also comprises the essentially clear liquid product obtained by reconstituting the solid product defined above, and a method of medical treatment which comprises administering to a patient the above essentially clear liquid comprising a stabilized nanodispersion or loaded micelle of the liquid biologically active agent.

The invention additionally comprises a device for producing solid formulations of liquid biologically active agents comprising
 a container,
 means for adding at leas one stabilizing agent and at least one solvent into the container,
 mixing means operable with the container to form a first mixture of the stabilizing agent and the solvent under conditions to achieve micelle or nanodispersion therein,
 means for subsequently adding a liquid biologically active agent to the first mixture and to form a second mixture,
 means operating the mixing means under conditions to treat the second mixture to load the micelle or nanodispersion with the biologically active agent, and
 means for treating the loaded micelle or nanodispersion to form a solid product containing the liquid biologically active agent intimately associated with the stabilizing agent and substantially free of the solvent.

Examples of suitable stabilizing agents include, but are not limited to amphiphilic polymers such as linear, branched or star-shaped block amphiphilic copolymers where the hydrophilic part may include at least one member selected from a group consisting of poly(ethylene oxide), poly(N-vinylpyrrolidone), poly(N-2-hydroxypropyl methacrylamide), poly(2-ethyl-2-oxazoline), poly(glycidol), poly(2-hydroxyethylmethacrylate), poly(vinylalcohol), polymethacrylic acid derivatives, poly(vinylpyridinium), poly((ammoniumalkyl)methacrylate), poly((aminoalkyl)methacrylate) and combinations and derivatives thereof; and wherein the hydrophobic segment may include at least one member which is selected from a group consisting of a poly(ester), poly(ortho ester), poly(amide), poly(ester-amide), poly(anhydride), poly(propylene oxide), poly(tetrahydrofuran) and combinations thereof.

The poly(ester) may be at least one member selected from a group consisting of poly(ε-caprolactone), poly(lactide), poly(glycolide), poly(lactide-co-glycolide), poly(hydroxy alkanoates) (e.g. poly (γ-hydroxybutyrate)), poly(δ-hydroxy valerate)), poly (β-malic acid), and derivatives thereof.

Other non-limiting illustrative examples of stabilizing agents may include at least one member selected from the group consisting of sodium lauryl sulfate, hexadecyl pyridinium chloride, polysorbates, sorbitans, poly(oxy ethylene) alkyl ethers, polyoxyethylene) alkyl esters and the like, including various combinations thereof.

Without limiting the scope of the present invention, suitable agents for incorporation into the nanodispersion or micelles produced in accordance with the teachings of the instant invention may include at least one anaesthetic agent, such as propofol, at a physiologically effective amount, preferably provided at a concentration of about 0.1% to 15%, preferably 1% to 10% (w/v), of propofol. Typically personal characteristics, including but not limited to age, weight and/or health dictate the physiologically effective amount, or dosage, necessary.

Suitable solvents or mixtures thereof will have the ability to solublize appropriate amounts of the stabilizing agent as well as appropriate amounts of liquid biological agent without denaturation or degradation of the liquid biological agent. Preferred solvents (or mixtures of solvents) should be removed during the lyophilization, spray-drying or the like process. While numerous solvents are capable of functioning in accordance with the process of the instant invention, non-limiting illustrative examples of such solvents include water, dextrose solution in water, saline, DMSO, DMF, dioxane, pyridine, pyrimidine, and piperidine, alcohols such as methanol, ethanol, n-butanol and t-butanol, and acetone, which are useful either alone or in combination, and may be further admixed, e.g. with water, to form a binary mixture. Other solvents may be added in small amounts to facilitate the dissolution of the drug.

Objectives and advantages of this invention will become apparent from the following description taken in conjunction with the accompanying drawings wherein are set forth, by way of illustration and examples, certain embodiments of this invention. The drawings constitute a part of this specification and include exemplary embodiments of the present invention and illustrate various objectives and features thereof.

DESCRIPTION OF PREFERRED EMBODIMENTS

Figure 20:
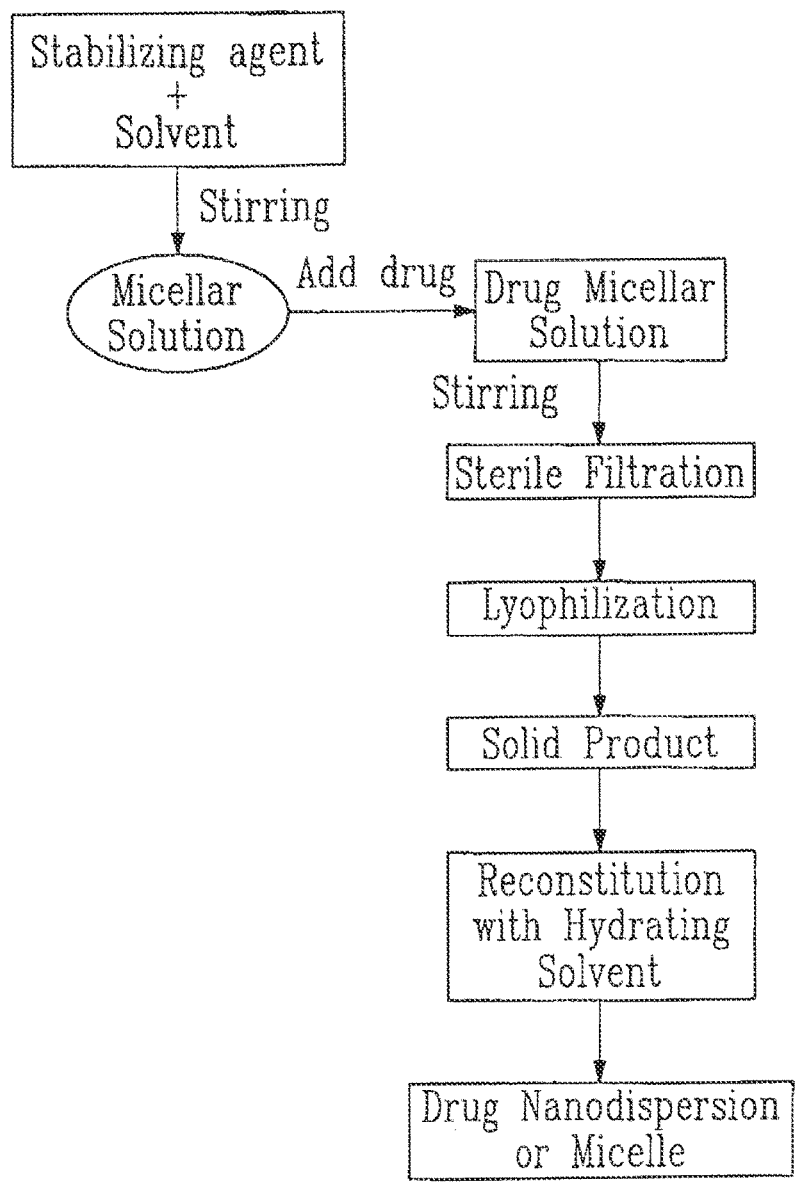
FIG. 20 is a schematic representation of a drug loading procedure and preparation of an essentially clear solution thereof according to the invention.

In accordance with the schematic representation set forth in FIG. 20, predetermined amounts of a stabilizing agent, e.g. a suitable polymer, copolymer or a surfactant or a dispersing agent, and optionally, an additive, e.g. a buffer, a cryoprotectant/a lyoprotectant/a bulk forming agent or the like (e.g. commercially available poly (vinylpyrrolidone) Kollidon 12 PF® or 17PF®, BASF) and/or additional stabilizing agents are dissolved in a solvent, e.g. water, an aqueous solution, at least one non-aqueous organic solvent, or combinations of water or an aqueous solution and said at least one non-aqueous organic solvent to form a first mixture in the form of a micellar solution. It has been realized that proper mixing achieves micelle or nanodispersion formation within the first mixture.

Once the first mixture is well formed, a liquid drug, here propofol, although any other liquid biologically active agent may be used as will be appreciated by one skilled in the art, is added to the first mixture under conditions well known to those skilled in the art, whereby the micelle or nanodispersion will be loaded with the liquid drug in a second mixture in the form of a drug micellar clear solution.

In either or both of the mixing steps described above, a suitable "additive" could be added for purposes well known to those skilled in the art. Non limiting examples of additives include, but are not limited to buffers, cryoprotectants, lyoprotectants, analgesics and bulk forming agents. Other suitable additives include, but are not limited to poly(vinylpyrrolidone), poly(ethylene glycol), sugars (lactose, trehalose), polyols (mannitol), saccharides and amino acids soluble in the solvent or solvent mixture. As broadly recited herein, the term "solvent" is understood to mean water alone, water with at least one non-aqueous organic solvent, or combinations of water and said at least one non-aqueous organic solvent. In one illustrative embodiment, additional dissolution enhancing means, here stirring, may be employed to aid in the forming of the liquid comprising a biologically active agent, a stabilizing agent and a solvent, prior to treatment to form a solid product. Illustrative, but non-limiting examples of said dissolution enhancing means may include a process, for example, wherein the mixture may be stirred, vortexed and sonicated, if needed. For some polymers, the solution may also need to be heated to speed up dissolution.

In the illustrated embodiment, the solution is filtered through a sterilizing filter, e.g. through a 0.2 µm filter. Subsequently, the solution is freeze-dried to form a sterile dry cake or powder or the like.

Lastly, for administration to a patient, the dried powder or cake is reconstituted with water, saline 0.9%, dextrose 5%, or other suitable solvent, or drug containing aqueous solutions, whereby a stable nanodispersion or loaded micelle is spontaneously produced.

The reconstituted formulation comprising nanodispersions or micelles in a suitable (usually aqueous) solvent may be characterized by;
1. Particle size and particle size distribution of the nanodispersion or micelle e.g. as determined by dynamic light scattering;
2. Clarity of the liquid e.g. as determined by degree of light transmittance at 660 nm;
3—pH;
4—Drug content/dose/concentration;
5—Viscosity (not in examples though);
6—Osmolality In the present invention, the drug loading levels of 1 to 10% w/w were found to produce clear/stable solutions at any volume of reconstitution from 10 mg/mL, (found in commercially available propofol emulsions), to 100 mg/mL. However, at the latter concentration, the solution's viscosity becomes an issue for injection. Hence, the concentration of polymer in water is the limiting factor for reconstitution volume of formulations.

Starting at around 12% drug loading level, reconstituted solutions, while remaining essentially clear, become increasingly opalescent, with a blue tint at 12% to a transparent, cloudy suspension at 20% and more. Nevertheless, all of these formulations of the instant invention were found to be stable for more than 24 hours, i.e. they do not precipitate upon dilution in water and/or albumin 35 g/L solutions. The opalescence suggests the swelling of the micelles to bigger sizes causing light diffraction observable by the naked eye.

The presence of albumin does not affect the stability of the propofol formulation of the current invention. Dilutions of 10, 20, and 40 mg/mL formulations at 5% w/w, 7% w/w, 10% w/w, and 15% w/w drug loading levels in 35 g/L albumin solutions showed no significant turbidity or differences with reconstituted solutions in water, saline or dextrose. That is, the clear solutions stayed clear, with no visible precipitation of polymer and/or albumin and/or floating propofol (phase separation is not present). Similarly, the opalescent suspensions stayed opalescent, but less so after dilution, with no precipitation of polymer and/or albumin and/or floating propofol.

Figure 21:
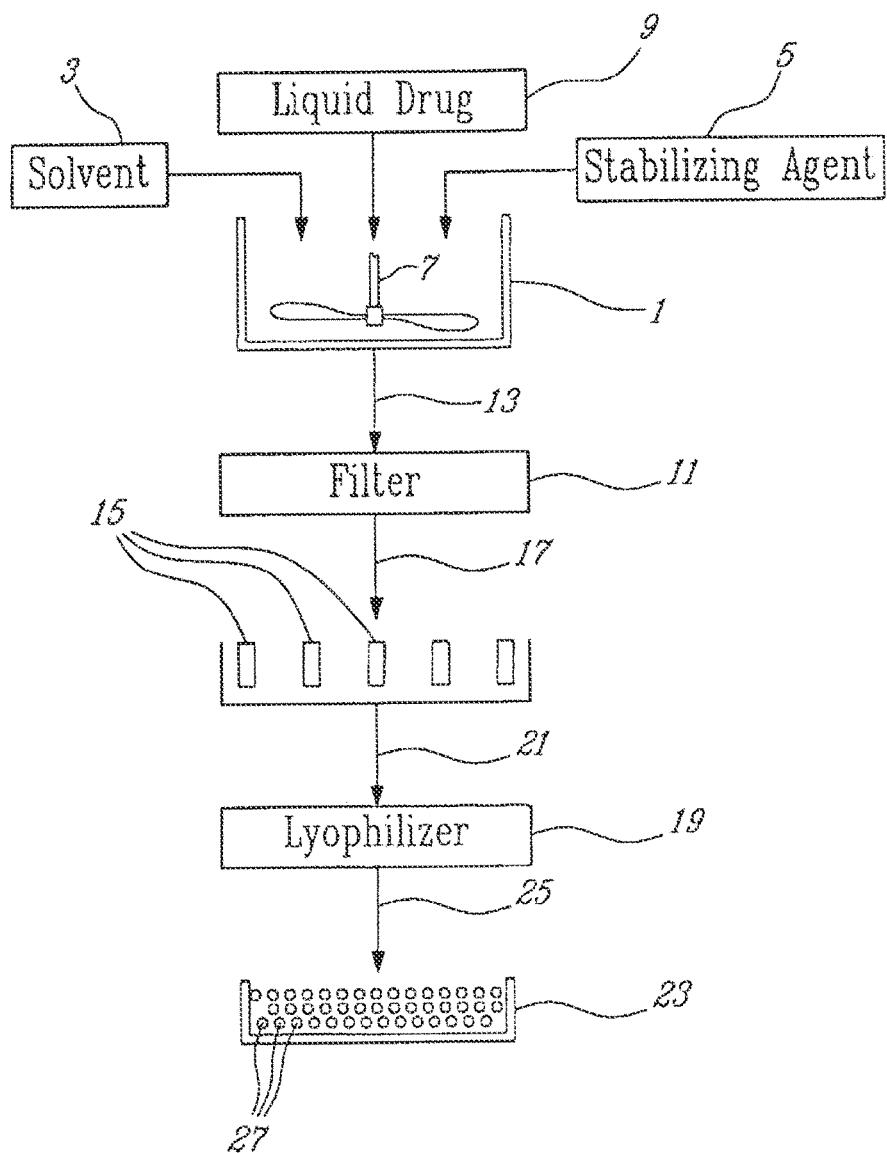
FIG. 21 is a schematic illustration of a device for producing a solid drug formulation according to the invention.

With reference to FIG. 21, a device for carrying out the preparation of a solid product according to the invention comprises a container 1 which is connected in known manner to a supply 3 of solvent, here water, and a supply 5 of a stabilizing agent, here PVP-PDLLA. A mixer 7 is provided in container 1 to stir the mixture of water and PVP-PDLLA under conditions for forming a micelle or nanodispersion.

A supply 9 of propofol is also connected in known manner to container 1 to add propofol thereto once micelle or nanodispersion is achieved through stirrer 7 thereby forming a second mixture comprising a micelle or nanodispersion loaded with propofol.

In the non limiting illustrated embodiment, there is provided a filter 11 allowing for sterilization of the micelle or nanodispersion, filter 11 being connected in known manner to container 1 through duct 13. Vials 15 are provided at 15 downstream of filter 11, to receive filtered quantities of sterilized micelle or nanodispersion. Vials 15 are connected in known manner through duct 17 to filter 11.

The device also comprises a lyophilizer 19 of known construction connected in known manner to vials 15 through duct 21 downstream of vials 15. A recipient 23 is finally connected to vials 15 through duct 25 to collect the solid product 27 obtained through lyophilization.

EXAMPLES

The invention will now be illustrated but is not limited by means of the following examples. The stabilizing agents used are different types of commercially available poly(N-vinylpyrrolidone)-b-poly(d,l-lactide) copolymers, while the liquid biologically active agent is propofol. It is understood that other stabilizing agents and liquid biologically active agents could also be used with similar results as will be appreciated by one skilled in the art.

Characteristics of PVP-PDLLA lots used in the following examples are given in Table 1.

TABLE 1

Characteristics of PVP-PDLLA lots used in the following examples

| PVP-PDLLA | PDLLA Wt %[1] | PDLLA mol %[1] | Mw[2] | Mn[2] | PDI |
|---|---|---|---|---|---|
| POLYMER 1 | 36.7 | 47.2 | 3900 | 3500 | 1.1 |
| POLYMER 2 | 38.1 | 48.8 | 4500 | 3900 | 1.2 |
| POLYMER 3 | 35.7 | 46.4 | 4961 | 4177 | 1.2 |
| POLYMER 4 | 36.7 | 47.2 | 4591 | 4012 | 1.1 |
| POLYMER 5 | 33.6 | 43.8 | 4685 | 3872 | 1.2 |

[1]Weight and molar percentages were measured from elemental analysis of polymer samples.
[2]Absolute molecular weights were determined using a Gel Permeation Chromatography system equipped with a light scattering detector.

Example 1

PVP-PDLLA (POLYMER 1 and POLYMER 2) samples were dissolved in mixtures of water and various amounts of tert-butyl alcohol (TBA). Propofol is then added to the PVP-PDLLA solution. Water is then added to the TBA/PVP-PDLLA/propofol solution to the desired final volume. Final TBA concentration in these solutions was 10-30%. Drug loading levels, % w/w of propofol/(propofol PVP-PDLLA), were also varied from 5, 7, 8, 10, 12, 15 and 20%. Solutions were then frozen in a dry ice/acetone bath and lyophilized for at least 24 hours. Lyophilized cakes obtained were then reconstituted by adding water to obtain an aqueous solution of propofol 1% w/v in less than 30 seconds. Overall results indicated that at 10% w/w drug loading levels and below, solutions were 100% homogeneous. At drug loading levels above 10% w/w, the solutions were gradually more and more opalescent (bluish tint caused by diffracted light). At 20%, solutions are cloudy, but stable (no precipitation for more than 8 hours).

Example 2

PVP-PDLLA (POLYMER 1) is dissolved directly in water at concentrations between 100 to 350 mg/mL. Propofol is added to the PVP-PDLLA solution and mixed until a homogenous solution is obtained. The solution is then diluted to a concentration of 1% w/v of propofol. 7, 10 and 12% w/w drug loading levels were tested. All solutions were then filtered using 0.2 μm sterile filters and frozen in acetone/dry ice bath or in −80° C. freezer for at least 4 hours before being lyophilized for 48 hours. Solid lyophilized cakes of 7, 10 and 12% w/w were reconstituted by adding water for injection. 7 and 10% w/w drug loading levels yield homogenous solutions, while the 12% w/w yielded a slightly opalescent solution (bluish tint). All where stable for more than 8 hours, i.e. no precipitation or phase separation under visual observation.

TABLE 2

Reconstituted formulation characteristics of example 1.

| Sample ID FR041124 | DLL theo (% w/w) | DLL exp (%) | Osmolality mOsm | Particle size[1] (nm) |
|---|---|---|---|---|
| POLYMER 1 | 7 | 6.7 | 438 | 23 (99%)* |
| POLYMER 1 | 10 | 9.6 | 355 | 26 (99%)* |
| POLYMER 1 | 12 | 11.4 | 342 | 20 (99%)* |

*size of main peak (intensity signal) and volume percentage occupied by the main peak. All were reconstituted in 5% Dextrose

Example 3

Formulations found in table 2 were tested in female Sprague-Dawley rats at a dose of 10 mg/kg. Injection time was 1 minute. All formulations prepared had a propofol concentration of 1% w/v, i.e. 10 mg/mL.

TABLE 3

Pharmacodynamic parameters of Diprivan versus three propofol polymeric micelle formulations in Sprague-Dawley rats.

| Formulation (n = 5) | % DLL | Onset of Sleep | Time of First Movement (min ± Std Dev) | Time of Righting Reflex (min ± Std Dev) | Time of Full Recovery (min ± Std Dev) |
|---|---|---|---|---|---|
| Diprivan ® | ca. 7% | <1 min | 8 ± 3.4 | 10.4 ± 2.7 | 19.2 ± 3.3 |
| FR041124-11 | 7% | <1 min | 8.7 ± 1.5 | 9.3 ± 1.5 | 17.7 ± 0.6 |
| FR041124-21 | 10% | <1 min | 10.2 ± 2 | 10.4 ± 2.1 | 17.4 ± 2.7 |
| FR041124-31 | 12% | <1 min | 9.8 ± 3.0 | 11.2 ± 1.9 | 18.2 ± 1.1 |

Figure 1:
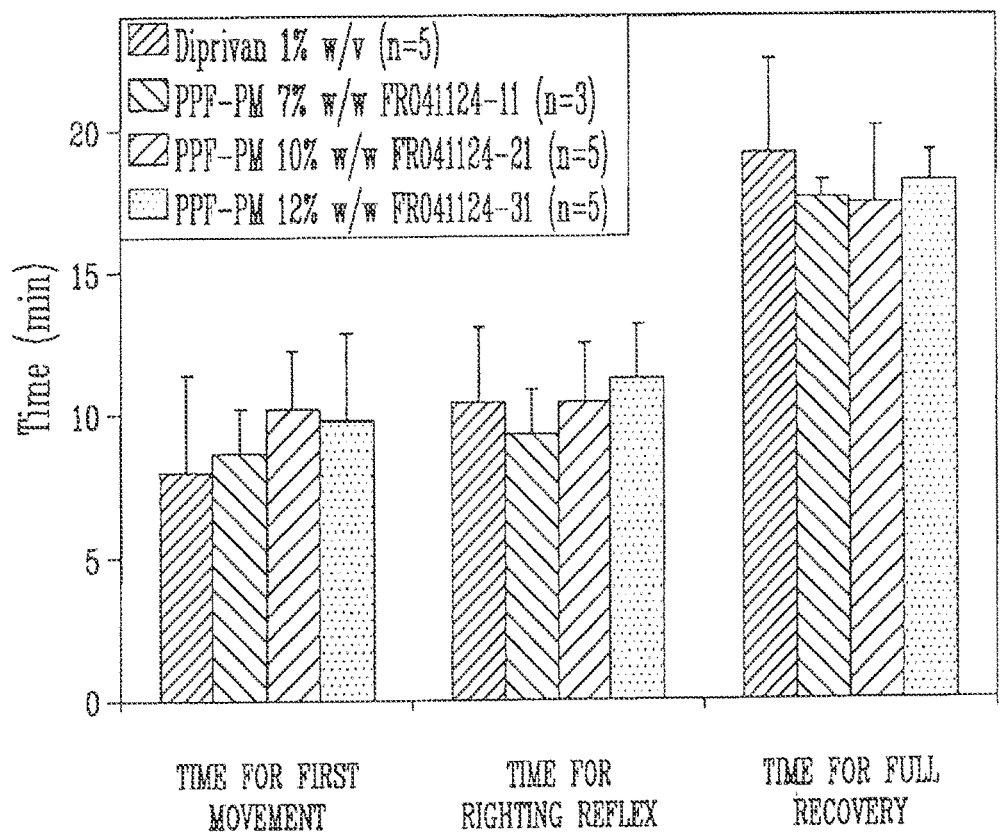
FIG. 1 is a graphical representation of pharmacodynamic effects obtained in vivo 001 (example 3) of Diprivan® versus three propofol polymeric micelle formulations after iv administration at 10 mg/kg in female Sprague-Dawley rats.

The results of the above study are illustrated in FIG. 1 which is a sleep/recovery study upon iv administration of 10 mg/kl of propofol formulation in rats (onset of sleep less than 1 min).

Example 4

PVP-PDLLA (POLYMER 2) is dissolved in water at concentrations between 100 to 350 mg/mL. Propofol is added to the PVP-PDLLA solution and mixed until a homogenous solution is obtained. The solution is then diluted to a concentration of 1% w/v of propofol. 7, 10 and 12% w/w drug loading levels were tested. All solutions were then filtered using 0.2 μm sterile filters and frozen in acetone/dry ice bath before being lyophilized for 48 hours. Solid lyophilized cakes of 7, 10 and 12% w/w were reconstituted by adding water. 7 and 10% w/w drug loading levels yielded homogenous solutions, while the 12% w/w yielded a slightly opalescent solution (feeble blue tint). All where stable for more than 8 hours, i.e. no precipitation or phase separation under visual observation.

Example 5

PVP-PDLLA (lot # POLYMER 3) is dissolved in water at concentrations between 100 to 350 mg/mL. Propofol is added to the PVP-PDLLA solution and mixed until a homogenous solution is obtained. The solution is then diluted to a concentration of 1% w/v of propofol. 7, 10 and 12% w/w drug loading levels were tested. All solutions were then filtered using 0.2 μm sterile filters and frozen in acetone/dry ice bath before being lyophilized for 48 hours. Solid lyophilized cakes of 7, 10 and 12% w/w were reconstituted by adding water. 7 and 10% w/w drug loading levels yielded homogenous solutions, while the 12% w/w yielded a slightly opalescent solution (feeble blue tint). All were stable for more than 8 hours, i.e. no precipitation or phase separation under visual observation.

Example 6

PVP-PDLLA (lot# POLYMER 2) is dissolved in sodium phosphate buffer pH 7.4. Propofol is added to the PVP-PDLLA solution and mixed until a homogenous solution is obtained. 10% drug loading level is tested. Water is then added to obtain a 1% w/v propofol concentration and a sodium phosphate buffer concentration ranging from 10 to 100 mM. Osmolality, pH and particle size of reconstituted solutions were obtained (table 4).

TABLE 4 pH, Osmolality and particle size as a function of sodium phosphate buffer concentration and time.

| Phosphate buffer conc. (mM) | Time after reconstitution hours | pH | Osmolality (mOsm) | Particle size (nm) |
|---|---|---|---|---|
| ca. 100 | 0 | 7.4 | 356 | 41 |
|  | ca. 24 | 7.1 | 369 | 36 |
| 75 | 0 | 7.3 | 323 | 35 |
|  | ca. 24 | 7.1 | 336 | 32 |
| 50 | 0 | 7.2 | 232 | 32 |
|  | ca. 24 | 6.9 | 241 | 30 |
| 10 | 0 | 6.5 | 105 | 29 |
|  | ca. 24 | 5.9 | 110 | 30 |

Example 7

PVP-PDLLA (lot # POLYMER 1, POLYMER 2, POLYMER 3, POLYMER 4 and POLYMER 5) is dissolved directly in 100 mM sodium phosphate buffer, pH 7.4, at concentrations between 100 to 350 mg/mL. Propofol is added to the PVP-PDLLA solution and mixed until a homogenous solution is obtained. The solution is then diluted to a concentration of 1% w/v of propofol and 70 mM of sodium phosphate buffer concentration. 7, 0.10 and 12% w/w drug loading levels were tested. All solutions were then filtered using 0.2 µm sterile filters and frozen in acetone/dry ice bath or in −80° C. freezer for at least 4 hours before being lyophilized for 48 hours. Solid lyophilized cakes of 7, 10 and 12% w/w were reconstituted by adding water for injection. 7 and 10% w/w drug loading levels yield homogenous solutions, while the 12% w/w yielded a slightly opalescent solution (bluish tint). All reconstituted solutions were stable for more than 24 hours, i.e. no precipitation or phase separation under visual observation. Characteristics of samples can be found in tables 5, 6 and 7.

TABLE 5

Formulation characteristics for lot # POLYMER 3 at 70 mM sodium phosphate buffer concentration

| + | DLL (%) w/w | pH | Osmolarity mOsm | Particle size[1] (nm) | Propofol Conc[2] (mg/mL) | % T (660 nm) |
|---|---|---|---|---|---|---|
| POLYMER 3 | 7 | 6.96 | 370 | 42 (100%) | 10.1 | 99.0 |
| POLYMER 3 | 10 | 7.05 | 292 | 39 (99.9%) | 9.9 | 98.6 |
| POLYMER 3 | 12 | 7.1 | 283 | 50 (99.3%) | 9.8 | 97.5 |

TABLE 6

Formulation characteristics for POLYMER 4 at 70 mM sodium phosphate buffer concentration

| Sample ID MT050816 | DLL (%) w/w | pH | Osmolarity mOsm | Particle size[1] (nm) | Propofol Conc[2] (mg/mL) | % T (660 nm) | Water content[3] (% w/w) |
|---|---|---|---|---|---|---|---|
| POLYMER 4 | 7 | 6.85 | 282 | 26.9 (100%) | 10.1 | 99.6 | 0.7 |
| POLYMER 4 | 10 | 6.94 | 243 | 26.1 (100%) | 10.2 | 98.9 | 0.9 |
| POLYMER 4 | 12 | 7.0 | 226 | 27.4 (100%) | 10.0 | 99.1 | 0.9 |

TABLE 7

Formulation characteristics for POLYMER 5 at 70 mM sodium phosphate buffer concentration

| Sample ID MT050809 | DLL (%) w/w | pH | Osmolarity mOsm | Particle size[1] (nm) | Propofol Conc[2] (mg/mL) | % T (660 nm) | Water content[3] (% w/w) |
|---|---|---|---|---|---|---|---|
| POLYMER 5 | 7 | 6.83 | 292 | 28.1 (100%) | 9.8 | 98.7 | 0.6 |
| POLYMER 5 | 10 | 6.93 | 248 | 29.5 (99.8%) | 9.4 | 98.8 | 0.8 |
| POLYMER 5 | 12 | 6.96 | 230 | 30.0 (99.0%) | 8.7 | 96.6 | 0.9 |

[1] Particle size measured using Malvern zeta sizer. Size is selected from the main peak of the intensity signal. Percentages in brackets represent the volume fraction of micelles of that main peak.
[2] Propofol concentration is determined by HPLC method.
[3] Water content is determined by Karl Fisher titration.

Example 8

PVP-PDLLA (POLYMER 4) is dissolved directly in 100 mM sodium phosphate buffer, pH 7.4, at concentrations between 140 to 300 mg/mL, depending on drug loading level. One of the two 10% w/w drug loading level formulations was dissolved in water. Propofol is added to the PVP-PDLLA solutions and mixed until homogenous solutions are obtained. The solutions are then diluted to a concentration of 1% w/v of propofol and 70 mM of sodium phosphate buffer concentration. 7, 10 and 12% w/w drug loading levels were tested. All solutions were then filtered using 0.2 μm sterile filters and frozen in −80° C. freezer for at least 4 hours before being lyophilized for 48 hours. Solid lyophilized cakes of 7, 10 and 12% w/w were reconstituted by adding water for injection, except for one formulation containing no phosphate buffer that was reconstituted in 5% dextrose w/w. All reconstituted solutions were stable for more than 24 hours, i.e. no precipitation or phase separation under visual observation.

Example 9

In-vivo 002. Using propofol-PM formulations presented in Example 8, and Diprivan® (commercial propofol 1% w/v formulation), a pharmacodynamic study was performed. The objectives of this study were:
1. Evaluate the pharmacodynamic effect of changing PVP-PDLLA molecular weight in the formulation
2. Evaluate the changes in pharmacodynamic parameters when using a sodium phosphate buffer to control pH and Osmolality
3. Compare results Lyophilized solid formulations of propofol-PM were reconstituted to a homogenous solution by adding water for injection (WFI) or dextrose 5% w/v for injection (sample MT050816-3). Final propofol concentration in solutions is 1%, equivalent to the commercial formulation Diprivan®. Female Sprague Dawley rats were injected a bolus dose of 10 mg/kg in 60 seconds. Pharmacodynamic parameters were then measured. Tables 8 and 9 present selected characteristics and parameters of interest.

Figure 2:
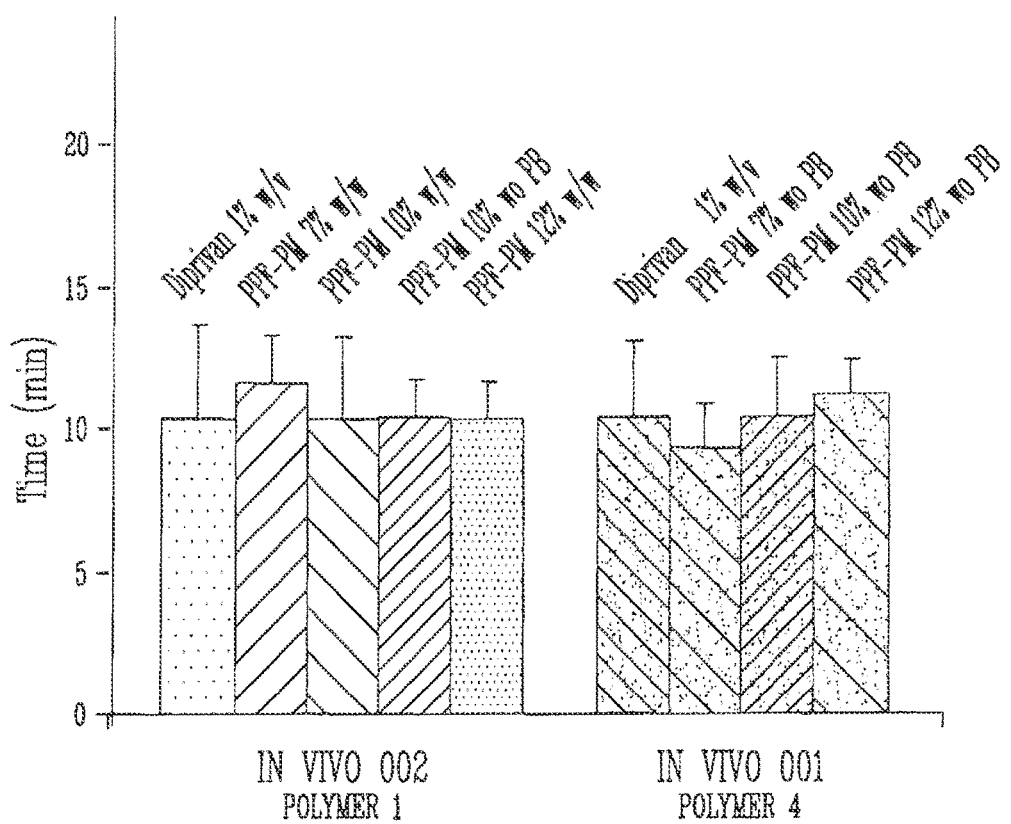
FIG. 2 is a graph showing the comparison of the time for righting reflex in pharmacodynamic study #1 (example 3) and #2 (example 9).
Figure 3:
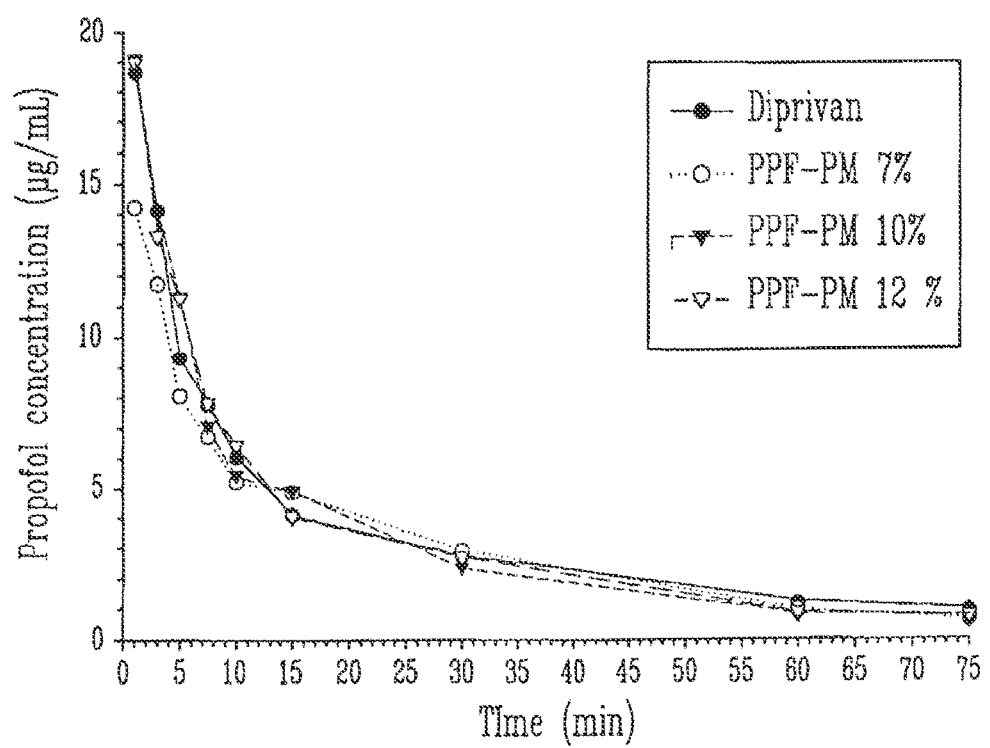
FIG. 3 is a graph showing the mean concentration-time profiles of propofol in blood following the intravenous administration of Diprivan® and three PPF-PM formulations (10 mg/kg).
Figure 4:
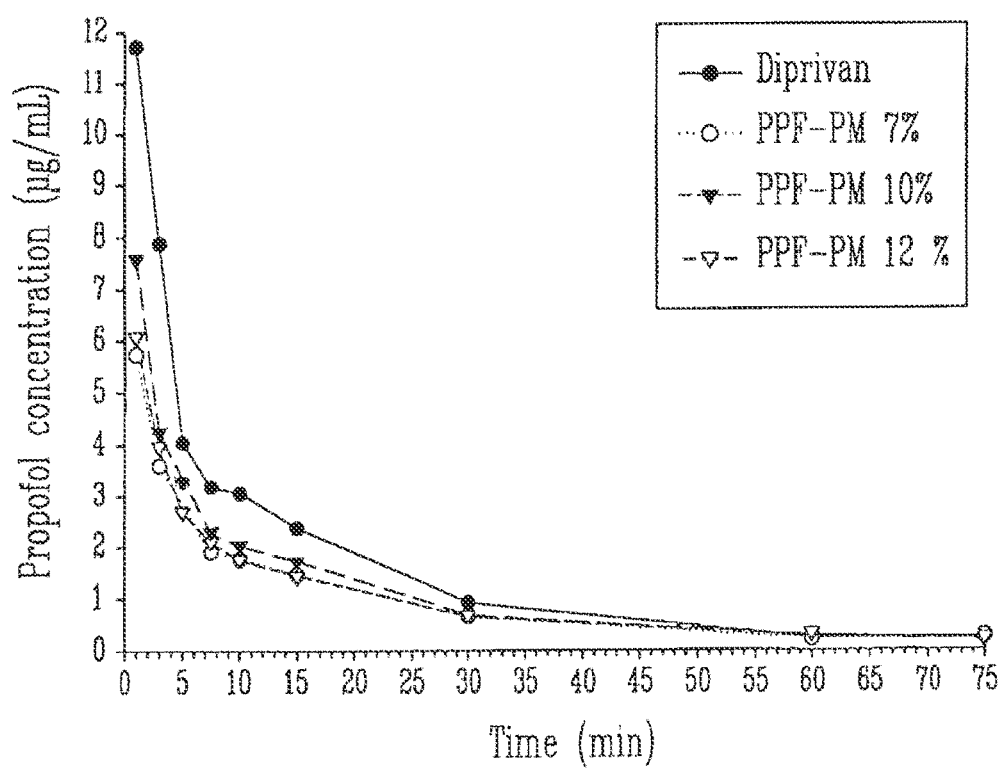
FIG. 4 is a graph showing the mean concentration-time profiles of propofol in plasma following the intravenous administration of Diprivan® and three PPF-PM formulations.
Figure 5:
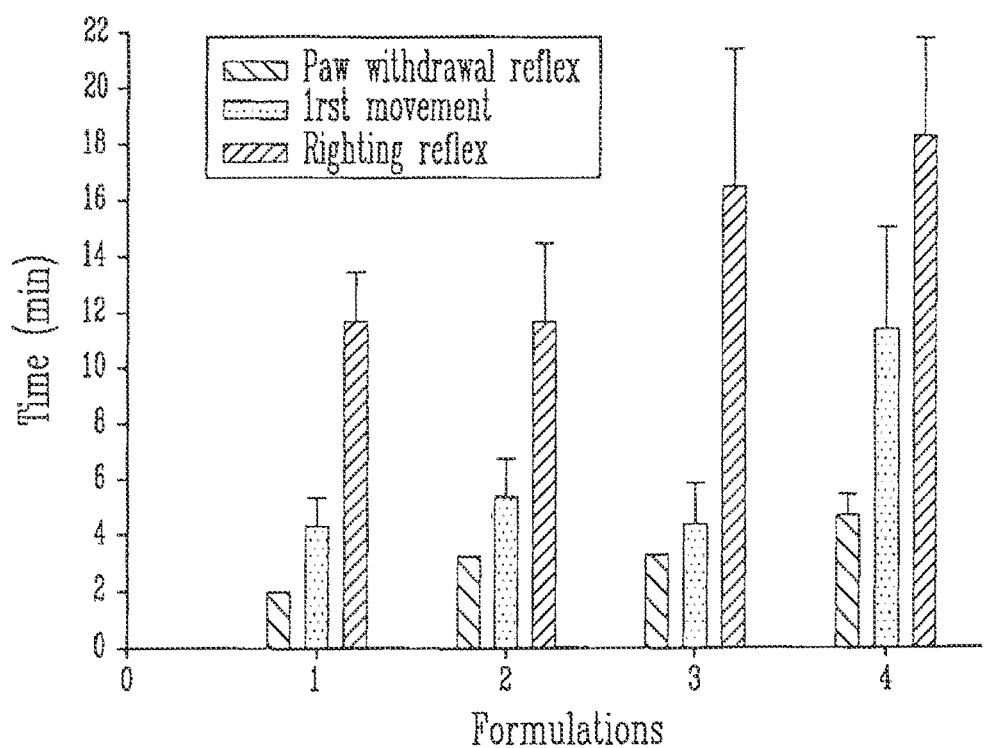
FIG. 5 is a graph showing the mean (±SD) withdrawal reflex time, time of first movement and time of righting following the intravenous administration of Diprivan®(1), PPF-PM 7%, PPF-PM 10% and PPF-PM 12% in male Sprague-Dawley rats obtained in vivo 003 study (example 10).
Figure 6:
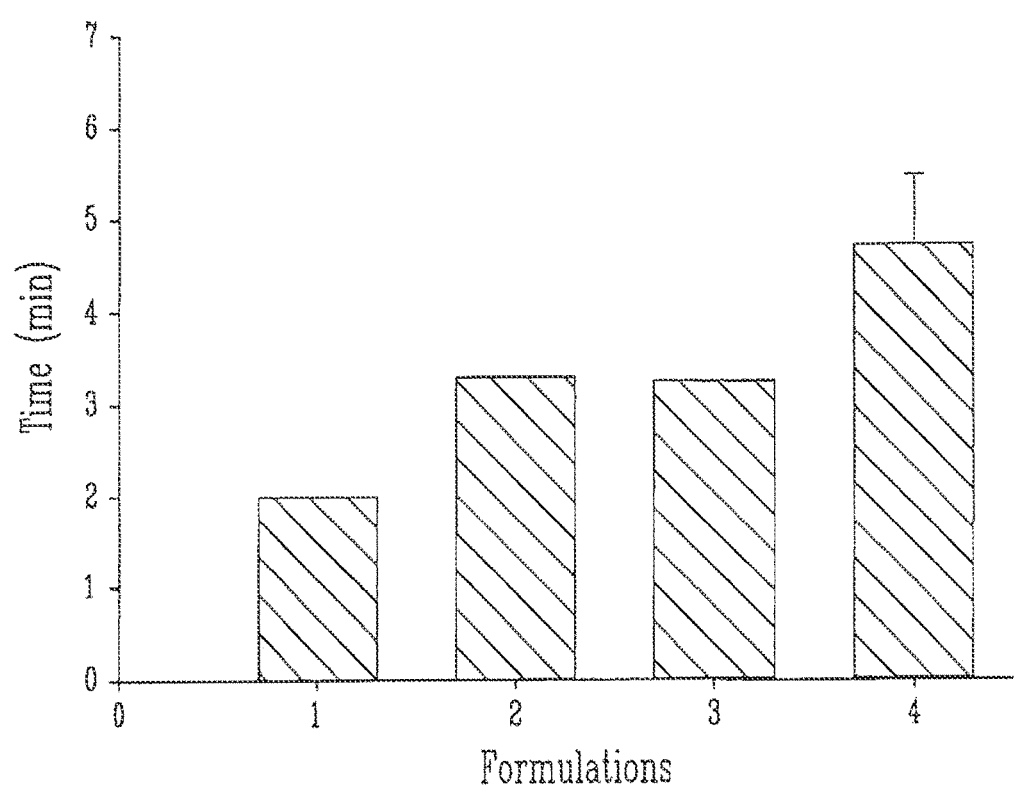
FIG. 6 is a graph showing the mean (±SD) pay withdrawal reflex time following the intravenous administration of Diprivan® (1), PPF-PM 7% (2), PPF-PM 10% (3) and PPF-PM 12% (4) in male Sprague-Dawley rats obtained in vivo 003 study (example 10).
Figure 7:
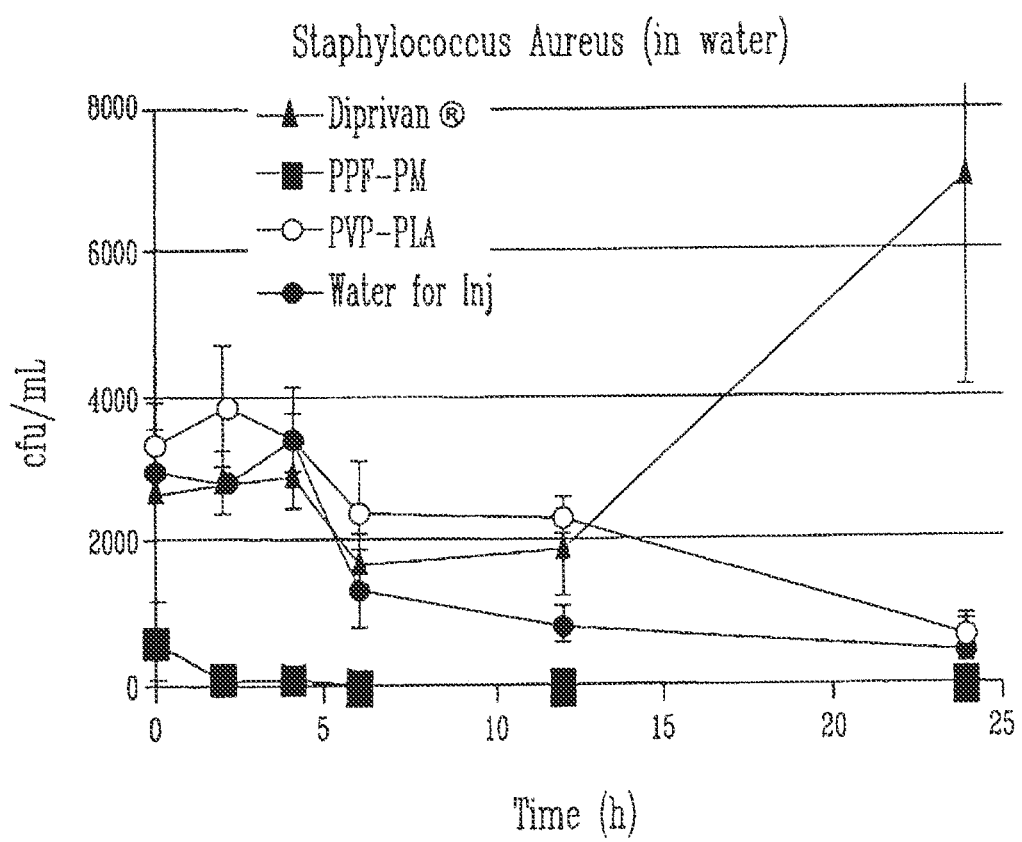
FIG. 7 is a graph showing *Staphylococcus Aureus* growth in water, in polymer solution in water, propofol polymeric micelle (PPF-PM) solution in water for injection and Diprivan®.
Figure 8:
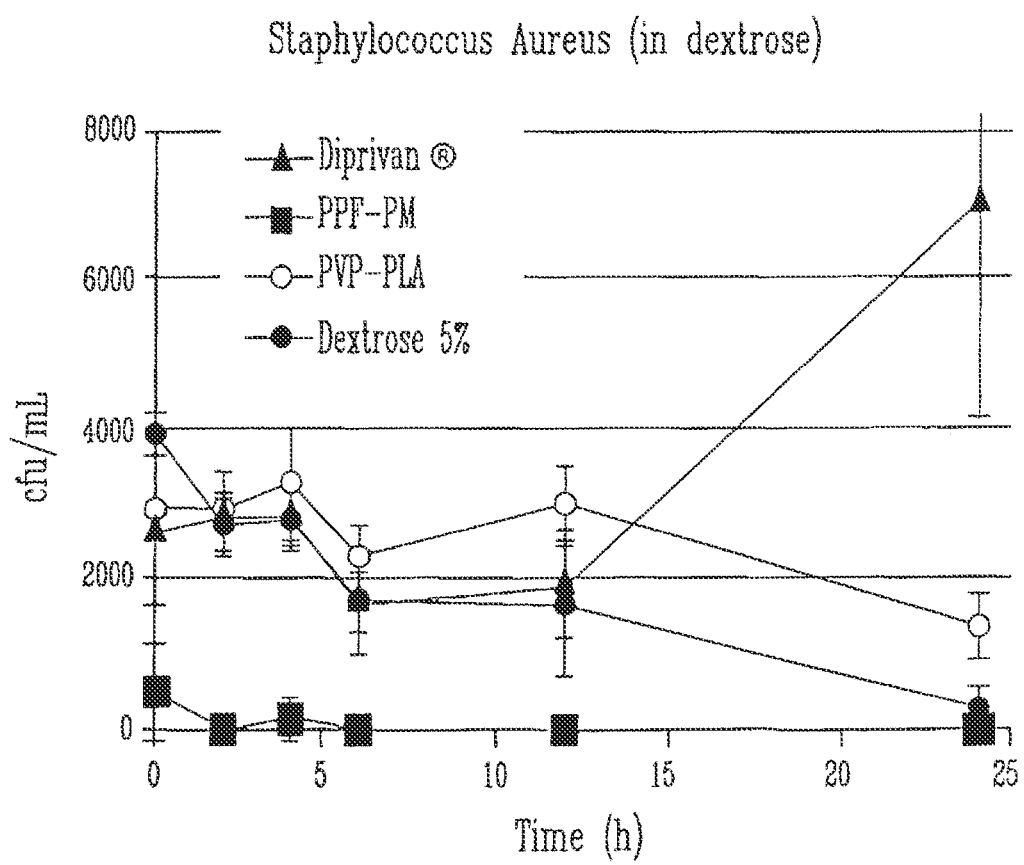
FIG. 8 is a graph showing *Staphylococcus Aureus* growth in dextrose, in polymer solution in dextrose (PVP-PLA), propofol polymeric micelle (PPF-PM) solution in dextrose and Diprivan®.
Figure 9:
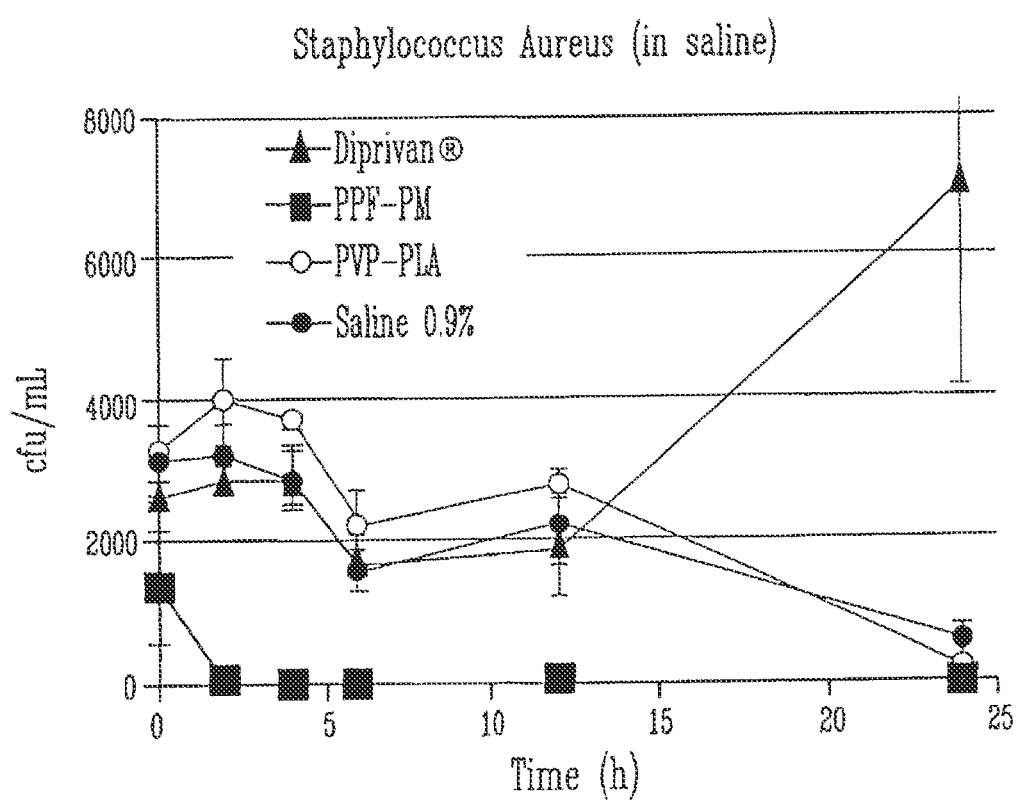
FIG. 9 is a graph showing *Staphylococcus Aureus* growth in saline, in polymer solution in saline (PVP-PLA), propofol polymeric micelle (PPF-PM) solution in saline and Diprivan®.
Figure 10:
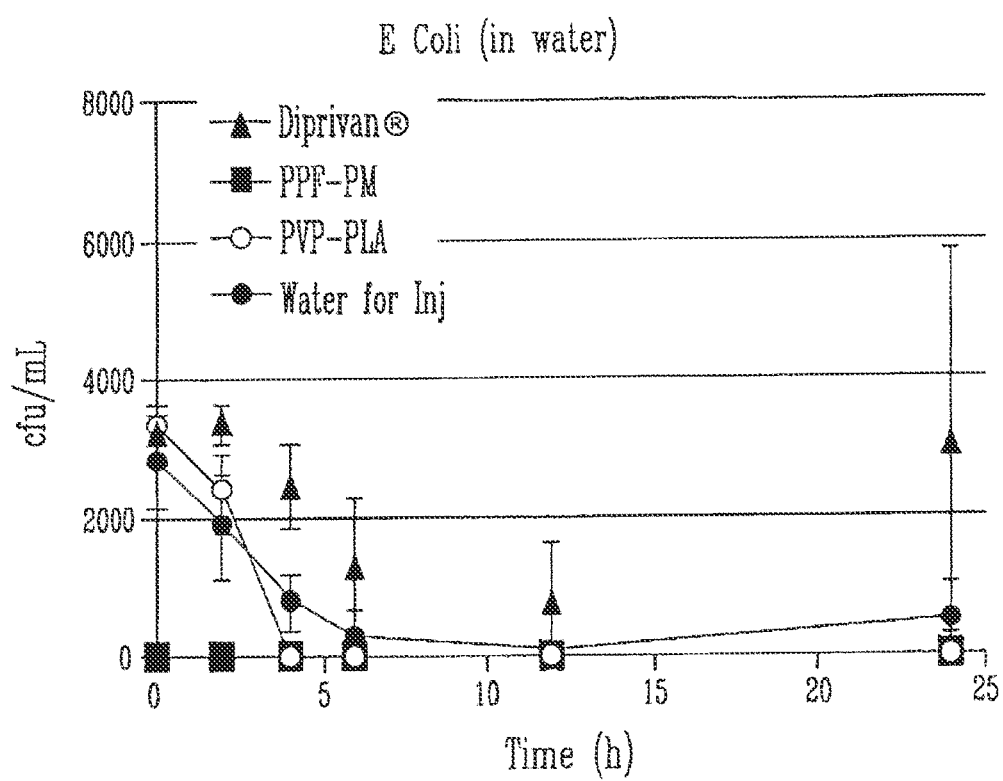
FIG. 10 is a graph showing E, *Coli* growth in water, in polymer solution in water (PVP-PLA), propofol polymeric micelle (PPF-PM) solution in water and Diprivan®.
Figure 11:
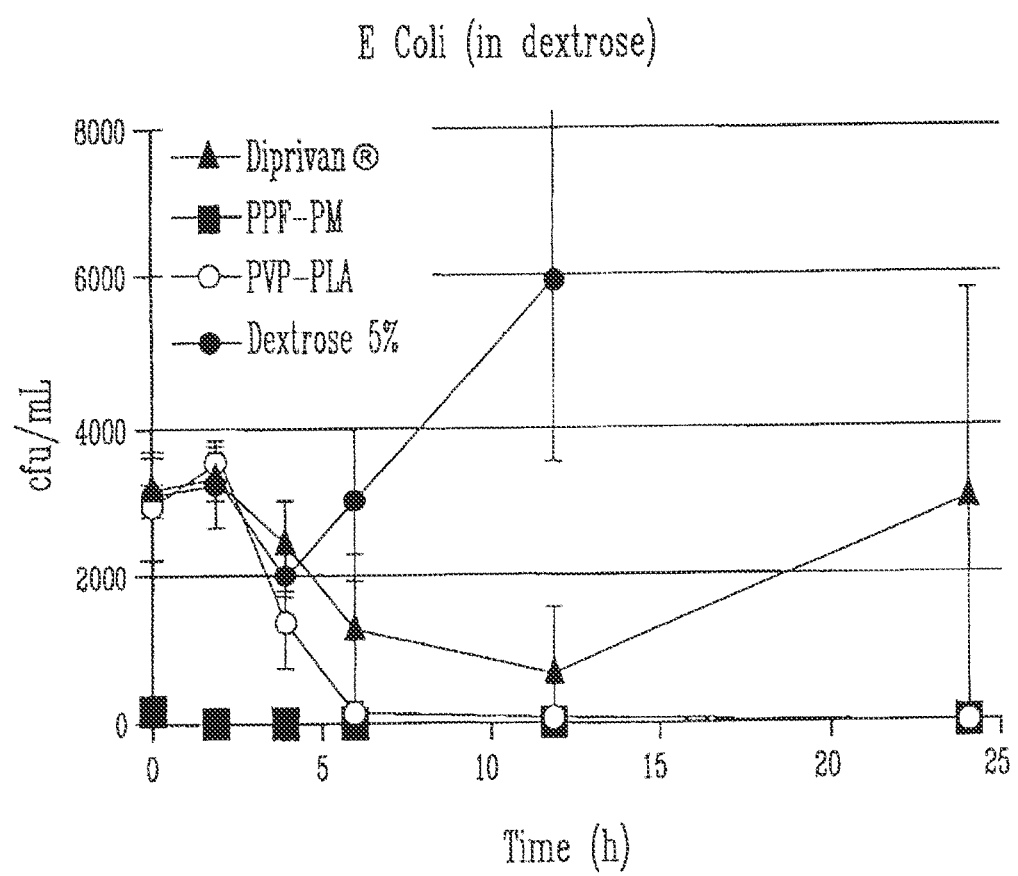
FIG. 11 is a graph showing *E. Coli* growth in dextrose, in polymer solution in dextrose (PVP-PLA), propofol polymeric micelle (PPF-PM) solution in dextrose and Diprivan®.
Figure 12:
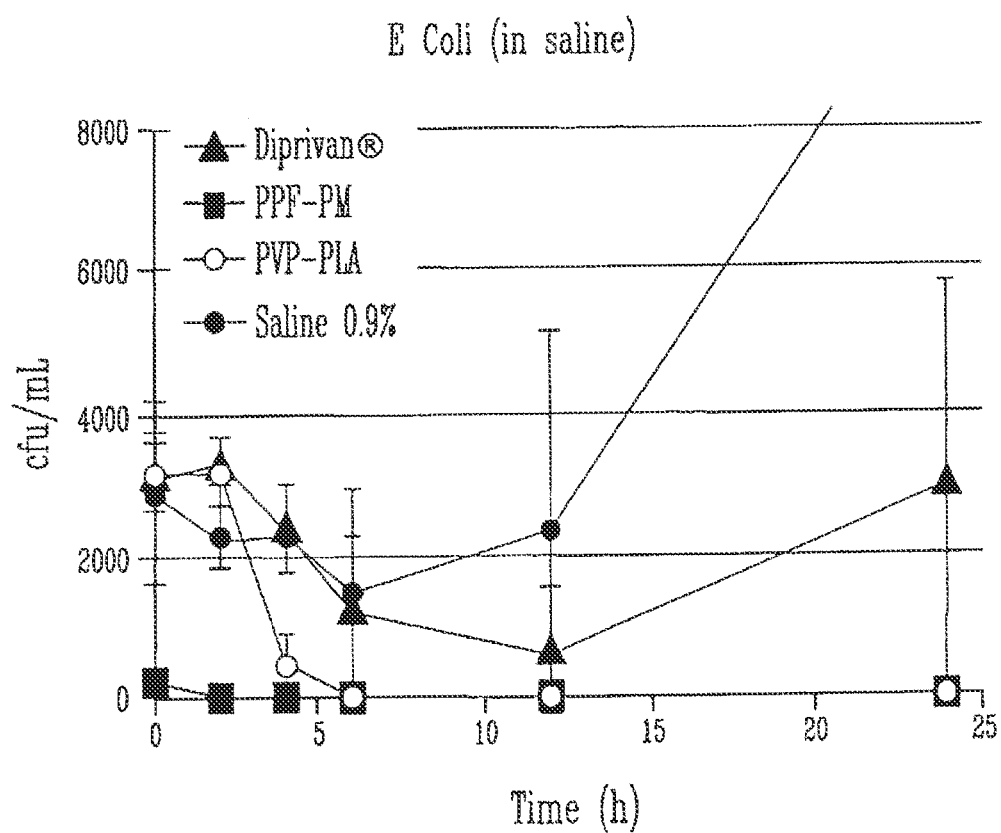
FIG. 12 is a graph showing *E. Coli* growth in saline, in polymer solution in saline (PVP-PLA), propofol polymeric micelle (PPF-PM) solution in saline and Diprivan®.
Figure 13:
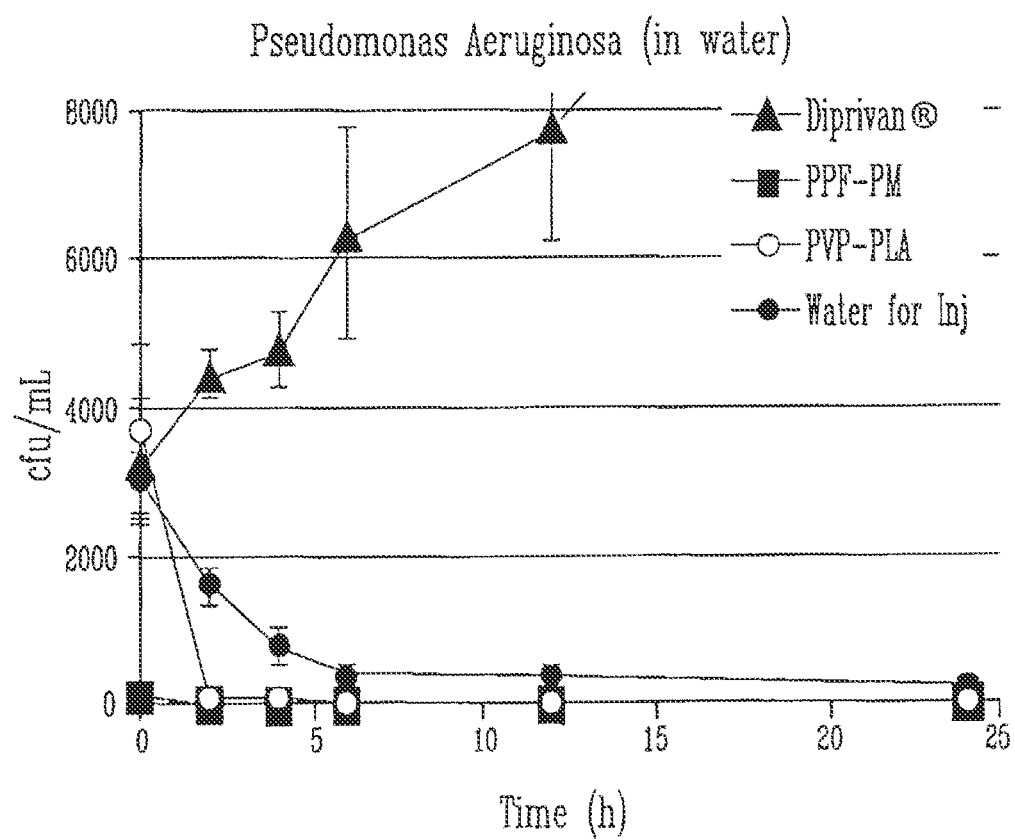
FIG. 13 is a graph showing *Pseudomonas Aeruginosa* growth in water, in polymer solution in water (PVP-PLA), propofol polymeric micelle (PPF-PM) solution in water and Diprivan®.
Figure 14:
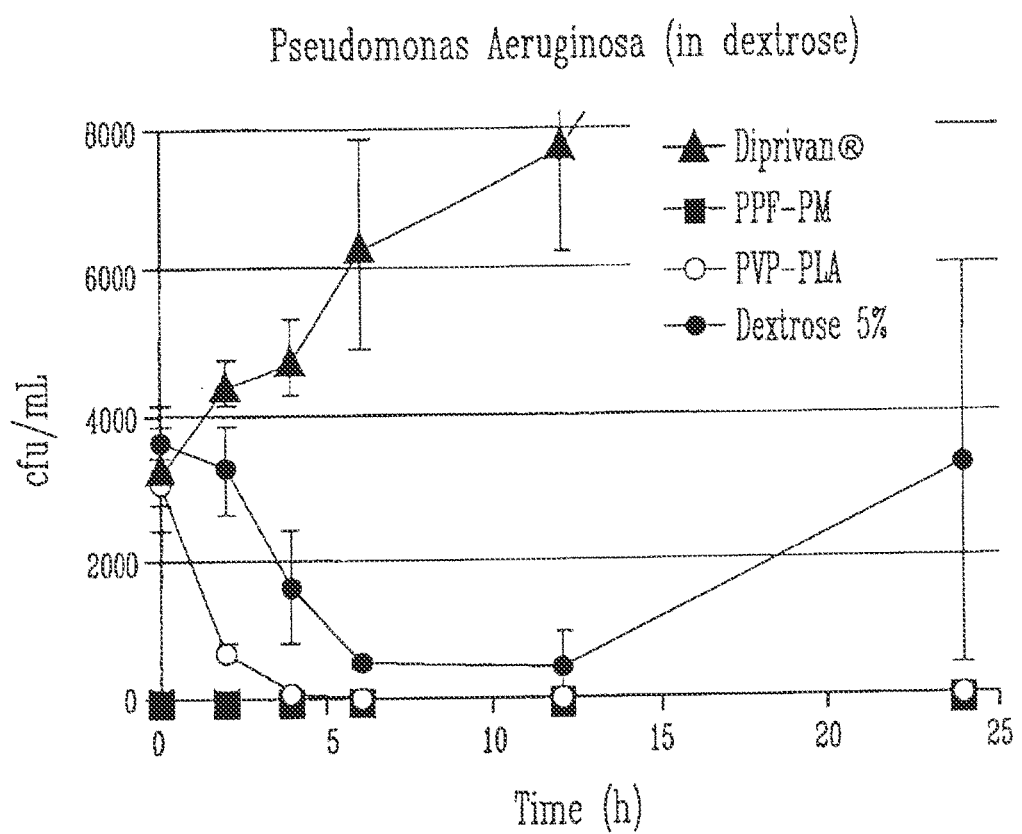
FIG. 14 is a graph showing *Pseudomonas Aeruginosa* growth in dextrose, in polymer solution in dextrose (PVP-PLA), propofol polymeric micelle (PPF-PM) solution in dextrose and Diprivan®
Figure 15:
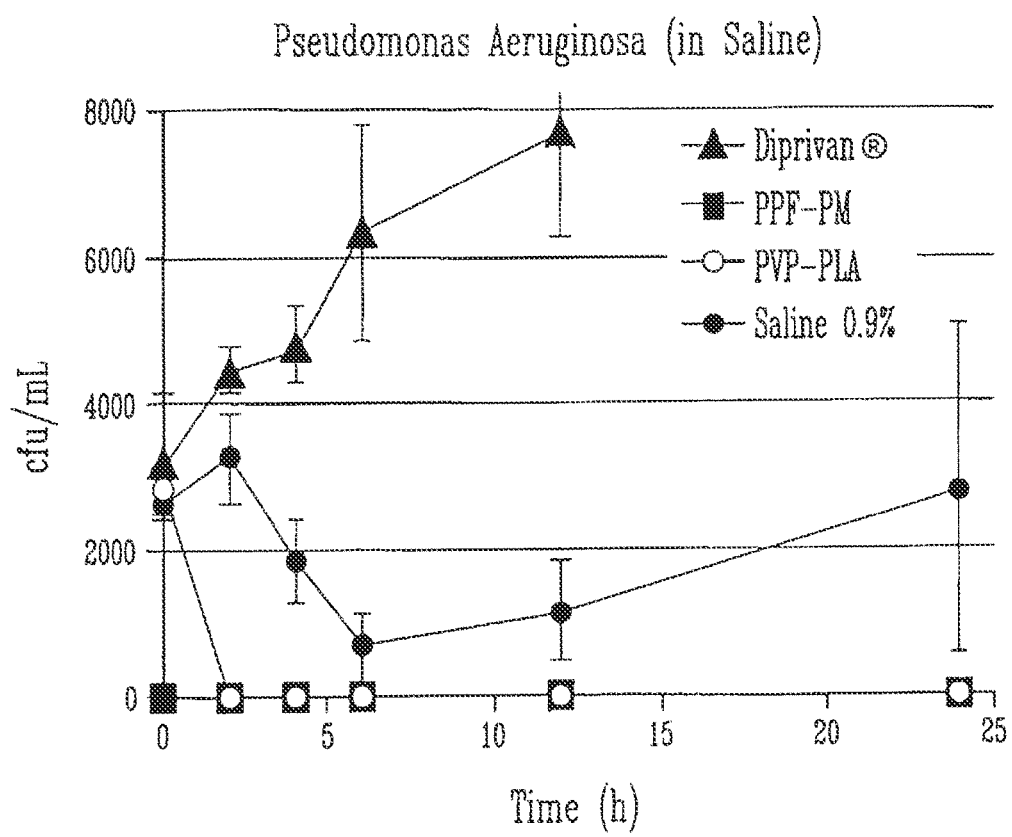
FIG. 15 is a graph showing *Pseudomonas Aeruginosa* growth in saline, in polymer solution in saline (PVP-PLA), propofol polymeric micelle (PPF-PM) solution in saline and Diprivan®.
Figure 16:
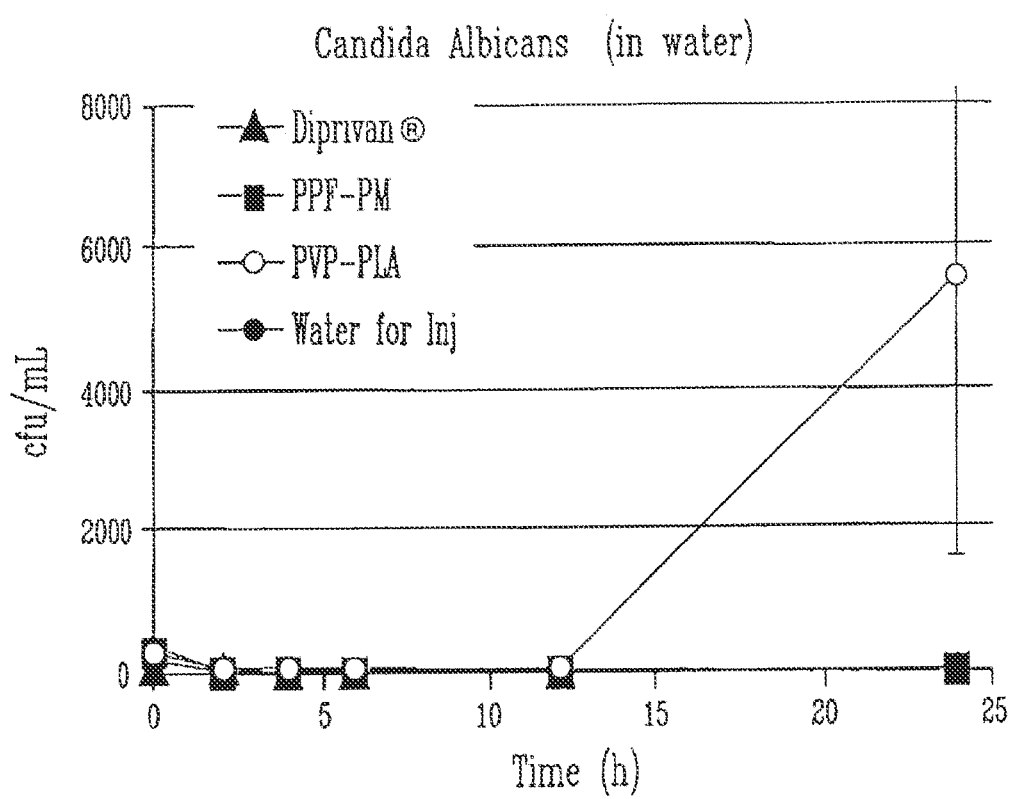
FIG. 16 is a graph showing *Candida Albicans* growth in water, in polymer solution in water (PVP-PLA), propofol polymeric micelle (PPF-PM) solution in water and Diprivan®.
Figure 17:
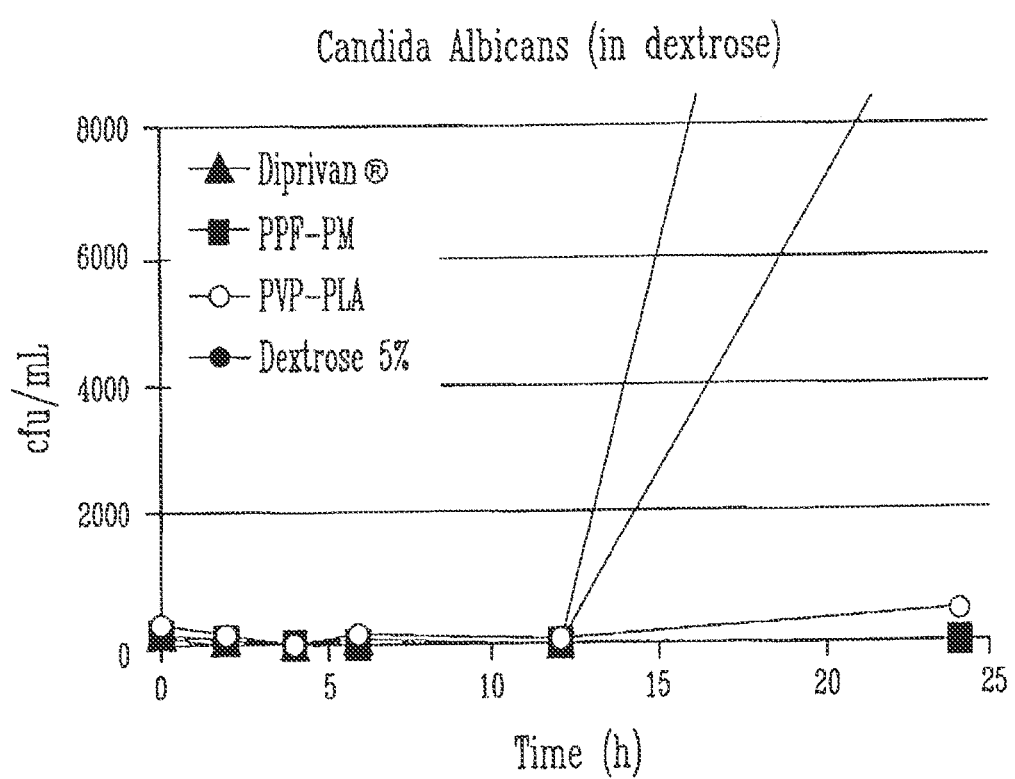
FIG. 17 is a graph showing *Candida Albicans* growth in dextrose, in polymer solution in dextrose (PVP-PLA), propofol polymeric micelle (PPF-PM) solution in dextrose and Diprivan®.
Figure 18:
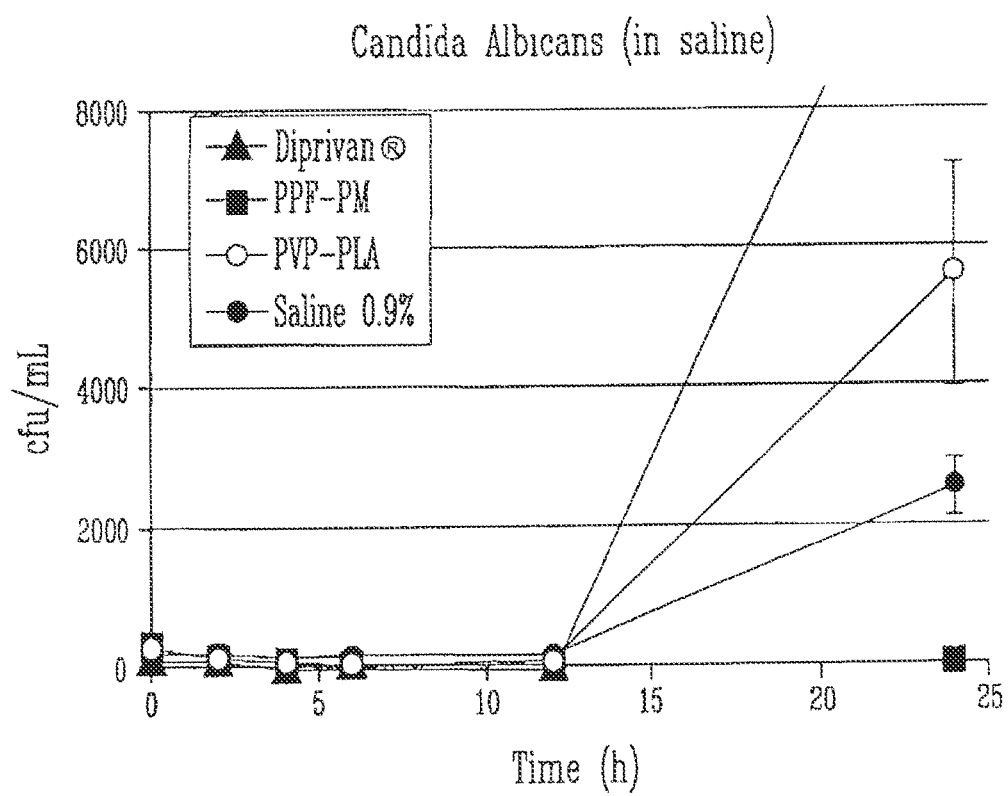
FIG. 18 is a graph showing *Candida Albicans* growth in saline, in polymer solution in saline (PVP-PLA), propofol polymeric micelle (PPF-PM) solution in saline and Diprivan®.
Figure 19A:
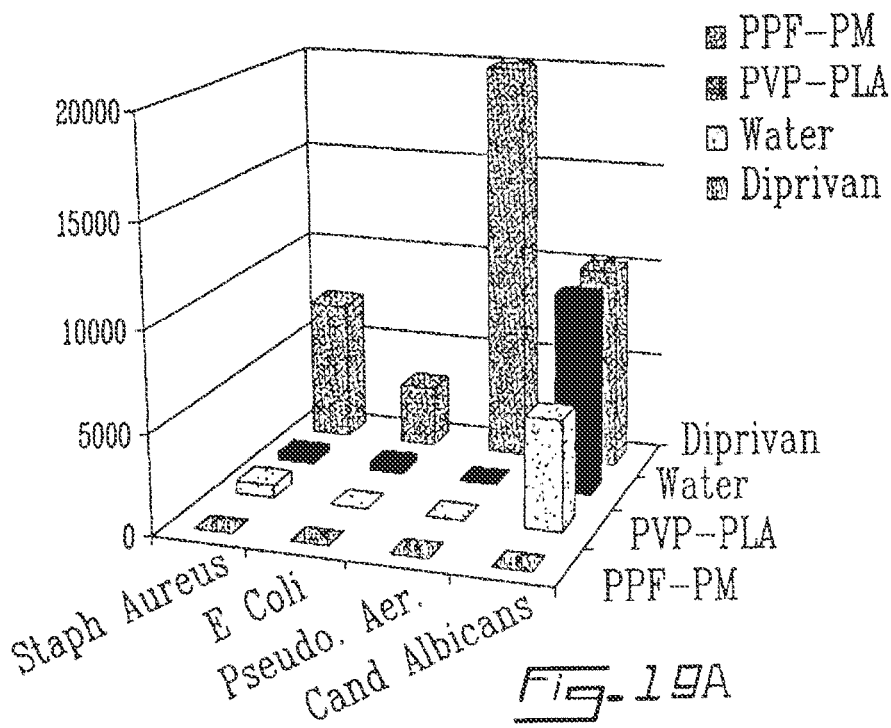
FIGS. 19A-C illustrate colony counts after 24 hour incubation time of all strains and all reconstitution media, polymer solutions and formulations.
Figure 19B:
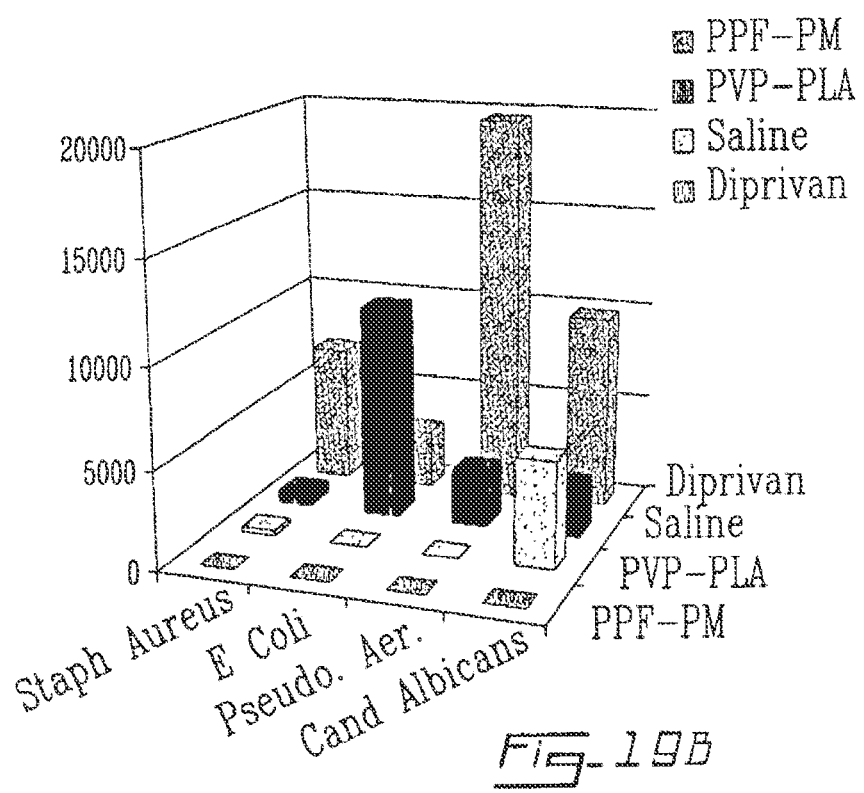
Figure 19C:
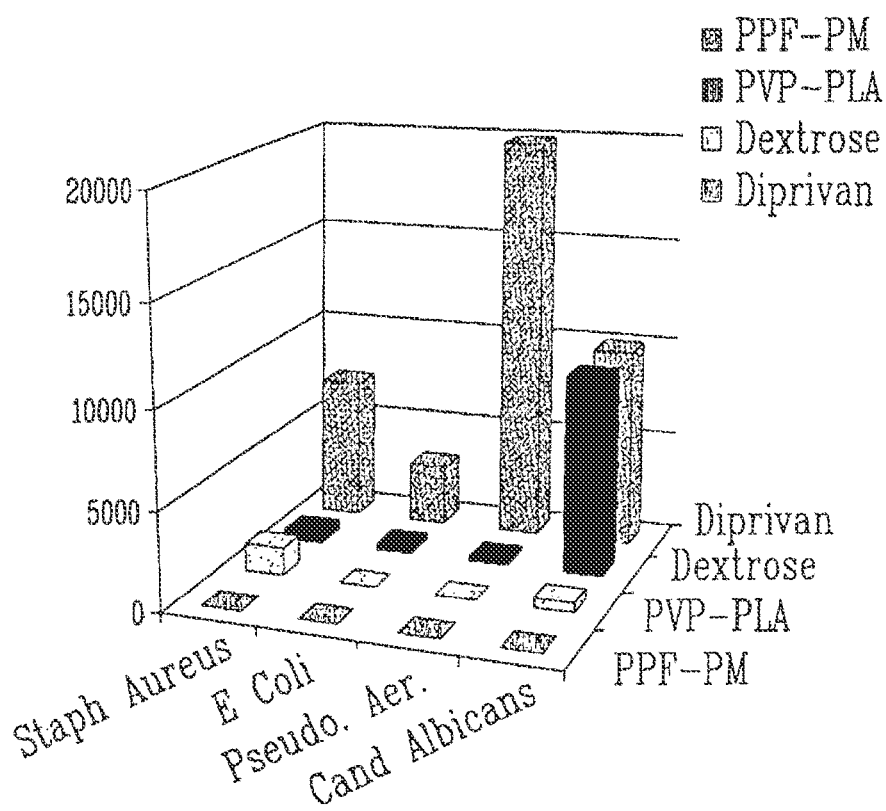

For a comparison of a time for righting reflex measured in in vivo 002 and in vivo 001 sleep/recovery study, reference is made to FIG. 2.

TABLE 8

In-house propofol-PM formulation compositions to be tested in second pharmacodynamic study.

| Lot# | Polymer batch# | % w/w DLL* | Final concentration of Phosphate Buffer (mM) | Reconstitution Medium | Speed | % T (660 nm) | propofol conc. (mg/mL) |
| --- | --- | --- | --- | --- | --- | --- | --- |
| MT050816-1 | POLYMER 4 | 7% | 70 | WFI | <1 min | 99.6 | 10.2 |
| MT050816-2 | POLYMER 4 | 10% | 70 | WFI | <1 min | 98.9 | 10.46 |
| MT050816-3 | POLYMER 4 | 10% | 0 | Dextrose 5% | <1 min | 98.9 | 9.9 |
| MT050817-4 | POLYMER 4 | 12% | 70 | WFI | <1 min | 99.1 | 10.26 |

*All parts percentages of drug loading reported herein are weight per unit weight (w/w), in which the weight in the denominator represents the total weight of the formulation (polymer and drug, excluding buffering excipients).

TABLE 9

In-house propofol-PM formulation compositions to be tested in second pharmacodynamic study: Characteristics and results

| Formulation (n = 5) | % DLL w/w | Micelle size* (nm) (Volume %) | pH | Osmolality mOsmol | % T (660 nm) | RESULTS Onset of Sleep | Time of Righting Reflex (min ± Std Dev) |
| --- | --- | --- | --- | --- | --- | --- | --- |
| Diprivan ® | Ca. 7% | ND | 7 | 311 | ND | <1 min | 10.4 ± 3.3 |
| MT050816-1 | 7% | 30.3 (100) | 6.86 | 284 | 99.6 | <1 min | 11.6 ± 1.7 |
| MT050816-2 | 10% | 31.5 (100) | 6.95 | 240 | 98.9 | <1 min | 10.4 ± 2.9 |
| MT050816-3 | 10% (no PB) | 37.6 (99.5) | 3.32 | 315 | 98.9 | <1 min | 10.4 ± 1.7 |
| MT050817-4 | 12% | 32.8 (99.95) | 7.02 | 224 | 99.1 | <1 min | 10.3 ± 1.3 |

*Particle size measured using Malvern zeta sizer. Size is selected from the main peak of the intensity signal. Percentages in brackets represent the volume fraction of micelles of that main peak.

Example 10

In-vivo 003. Using formulations prepared according to the protocol in example 8, pharmacokinetic and pharmacodynamic studies were performed in Male Sprague-Dawley rats. Formulations tested and pharmacokinetic study design, which included Diprivan®, are presented in the table below.

TABLE 10

Pharmacokinetic groups and details

| Group | Formulation | Dose (mg/kg) | Dose volume (mL/kg) | Injection time (sec) | Number of Animals | Matrix |
|---|---|---|---|---|---|---|
| 1 | Diprivan ® | 10 | 1 | 30 | 5 | Blood |
| 2 | | | | | 5 | Plasma |
| 3 | Propofol-PM (7% w/w) | 10 | 1 | 30 | 5 | Blood |
| 4 | | | | | 5 | Plasma |
| 5 | Propofol-PM (10% w/w) | 10 | 1 | 30 | 5 | Blood |
| 6 | | | | | 5 | Plasma |
| 7 | Propofol-PM (12% w/w) | 10 | 1 | 30 | 5 | Blood |
| 8 | | | | | 5 | Plasma |

Forty male Sprague-Dawley Rats (300-325 g) were used to determine the pharmacokinetic properties The animals were equally allotted into four groups (n = 5) A, B, C and D corresponding to the four treatments Diprivan ®, Propofol-PM 7%, 10% and 12% (w/w).

TABLE 11

Summary of mean pharmacokinetic parameters for propofol in blood for Diprivan ® and PPF-PM formulations

| PK parameters | Units | Diprivan ® | PPF-PM 7% w/w | PPF-PM 10% w/w | PPF-PM 12% w/w |
|---|---|---|---|---|---|
| $C_{max}$ | µg/mL | 18.65 | 14.4 * | 19.1 | 19.0 |
| $C_0$ | µg/mL | 20.4 | 14.1 | 21.7 | 18.5 |
| AUC t | µg · min/mL | 262.3 | 246.6 | 255.6 | 258.1 |
| AUC inf | µg · min/mL | 301.1 | 271.5 | 272.8 | 282.9 |
| CL | mL/min/kg | 31.3 | 28.4 | 22.5 | 25.4 |
| MRT | Min | 34.1 | 39.6 | 37.1 | 36.6 |
| T ½ | Min | 28.6 | 22.5 | 20.0 | 22.9 |
| T ½ α | Min | 3.1 | 2.6 | 2.9 | 3.0 |
| T ½ β | Min | 40.9 | 24.7 | 37.8 | 26.0 |
| $\lambda_1$ | /min | 0.262 | 0.303 | 0.349 | 0.245 |
| $\lambda_2$ | mL/kg | 0.024 | 0.032 | 0.027 | 0.028 |
| $V_1$ | µg/mL | 447.8 | 608.5 | 400.1 | 452.6 |
| Vss | µg/mL | 1347.9 | 1119.0 | 833.0 | 921.7 |

\* $p < 0.05$

TABLE 12

Summary of mean plasmatic pharmacokinetic parameters for Diprivan and PPF-PM formulations

| PK parameters | Units | Diprivan ® | PPF-PM 7% w/w | PPF-PM 10% w/w | PPF-PM 12% w/w |
|---|---|---|---|---|---|
| $C_{max}$ | µg/mL | 11.7 | 6.0 *** | 7.6 | 6.1 *** |
| $C_0$ | µg/mL | 12.4 | 6.2 | 6.6 | 6.8 |
| AUC t | µg · min/mL | 126.5 | 77.3 **** | 84.2 *** | 76.7 **** |
| AUC inf | µg · min/mL | 132.8 | 87.2 *** | 89.2 **** | 85.4 *** |
| CL | mL/min/kg | 19.2 | 27.2 *** | 21.9 | 28.3 |
| MRT | Min | 77.1 | 122.5 *** | 113.0 **** | 130.9 ** |
| T ½ | Min | 17.5 | 23.8 **** | 19.5 | 26.1 |
| T ½ α | Min | 1.4 | 3.5 * | 2.0 | 3.1 |
| T ½ β | Min | 16.6 | 38.7 | 20.3 | 32.2 * |
| $\lambda_1$ | /min | 0.508 | 0.243 *** | 0.432 | 0.287 * |
| $\lambda_2$ | mL/kg | 0.042 | 0.024 *** | 0.038 | 0.024 **** |
| $V_1$ | µg/mL | 626.0 | 1875.0 **** | 1052.9 * | 1622.0 **** |
| Vss | µg/mL | 1467.5 | 3293.3 **** | 2481.9 *** | 3632.1 **** |

\* $p < 0.05$
\*\* $p < 0.03$
\*\*\* $p < 0.02$
\*\*\*\* $p < 0.01$

TABLE 13

Mean partition coefficient (Kp RBC: Plasma) of propofol in blood following a single intravenous dose (target 10 mg/kg) of Diprivan® and 3 PPF-PM formulations (7, 10 and 12%)

| Time (min) | Kp Diprivan® | Kp PPF-PM 7% w/w | Kp PPF-PM 10% w/w | Kp PPF-PM 12% w/w |
|---|---|---|---|---|
| 1 | 8.5 | 10.4 | 14.0 | 15.7 |
| 3 | 7.6 | 9.9 | 12.0 | 11.3 |
| 5 | 6.4 | 5.8 | 9.8 | 10.5 |
| 7.5 | 5.6 | 5.9 | 5.9 | 7.0 |
| 10 | 3.7 | 4.2 | 4.2 | 5.7 |
| 15 | 2.1 | 4.1 | 3.9 | 3.2 |
| 30 | 2.2 | 2.7 | 2.1 | 2.5 |
| 60 | 1.1 | 0.9 | 0.6 | 0.7 |
| 75 | 0.8 | 0.5 | 0.5 | 0.6 |

Example 11

PVP-PDLLA (POLYMER 1) was dissolved directly in water at concentrations between 140 to 350 mg/mL. Propofol is added to the PVP-PDLLA solution and mixed until a homogenous solution is obtained. The solution is then diluted to a concentration of 1% w/v of propofol (7%, 9%, 10% and 12% w/w drug loading levels), The solutions were then filtered using 0.2 µm sterile filters and frozen in ethanol/dry ice bath before being lyophilized for 48 hours. Solid lyophilized cakes were reconstituted by adding sterile dextrose 5% for injection to yield a propofol concentration of 1% w/v (10 mg/mL). Micelle size distributions were then measured at 1% w/v and 0.1% w/v propofol concentrations to evaluate the effect of dilution. At 0.01% w/v (1/100 dilution), the light scattering signal was very weak for obvious reasons. The sample at 7% w/w drug loading level was the only one measured at 0.01% w/v-propofol concentration. All solutions were stable visually and no phase separation or precipitation was observed upon dilution. Characteristics of these formulations are presented in the table below.

TABLE 14

Characteristics and, particle size and stability, of propofol polymeric micelle formulations upon dilution

| Sample ID | DLL POLYMER 1 (%) w/w | Dilution medium | Micelle Size (nm) 1% w/v PPF | 0.1% w/v | 0.01% w/v |
|---|---|---|---|---|---|
| FR041124 | 7 | Dextrose 5% | 23 (99.4%) | 23 (99.4%) | 18 (100%) |
| DLG041123 | 9 | Dextrose 5% | 24 (99.6%) | 24 (99.9%) | ND |
| DLG041123 | 10 | Dextrose 5% | 24 (99.5%) | 25 (99.6%) | ND |
| DLG041123 | 12 | Dextrose 5% | 26 (97%) | 30 (98.6%) | ND |

Example 12: Microbial Growth Study

Formulations prepared as per example 2 were reconstituted in three different media (water for injection, dextrose 5% w/v and saline 0.9% w/v) inoculated with 4 different strains of bacteria. Furthermore, reconstitution media alone (saline, dextrose 5% and water for injection) and polymer solutions without any propofol in all three different reconstitution media were also inoculated for comparison, $1 \times 10^4$ cfu/mL were added to each articles tested (solutions, formulations, media). Dirpivan® emulsion was also inoculated for comparison. Characteristics of polymer solutions and formulations follow (table) and graphical results on microbial proliferation in different tests are presented below.

TABLE 15

Characteristics of formulation and polymer solutions tested for microbial growth study.

| Formulation | Propofol DLL (%) w/w | Reconstitution Medium | Time | Clarity | Conc. (mg/mL) |
|---|---|---|---|---|---|
| POLYMER 1 PVP-PLA | 0 | WFI | <30 sec | Clear | 0 |
| PVP-PLA | 0 | Dextrose | <30 sec | Clear | 0 |
| PVP-PLA | 0 | 0.9% Saline w/v | <30 sec | Clear | 0 |
| PPF-PM | 10 | WFI | <30 sec | Clear | 9.56 |
| PPF-PM | 10 | Dextrose | <30 sec | Clear | 9.72 |
| PPF-PM | 10 | 0.9% Saline w/v | <30 sec | Clear | 9.89 |

Results of the microbial growth study indicate that the PVP-PLA solutions of the invention (containing no propofol) are most of the time not significantly different than proliferation observed in the reconstitution media (water for injection, saline 0.9% w/v and dextrose 5% w/v) alone. The addition of propofol to form the propofol polymeric micelle (PPF-PM) formulations demonstrates that the intrinsic bactericidal property of propofol is active in killing all bacteria inoculated, independent on the reconstitution media or the polymer. Diprivan® as shown highest microbial growth support in all cases.

FIGS. 7-18: Microbial growth time profile of polymer solutions (PVP-PLA), propofol polymeric micelle formulations (PPF-PM), Diprivan® and reconstitution media of all 4 strains of bacteria tested.

Example 12

PVP-PDLLA (POLYMER 4) is dissolved directly in 100 mM sodium phosphate buffer, pH 7.4. Propofol is added to the solution and mixed. Once the clear solution is obtained, the solution is diluted to 1% w/v propofol concentration and a final buffer concentration of 75 mM. The solutions were then lyophilized. The freeze dried cakes were then reconstituted directly with 2%, 1% and 0.2% w/v lidocaine solutions. Particle size and pH of solutions were measured daily over a period of 5 days. Results are presented below.

TABLE 16

Propofol polymeric micelle stability in solution
with different lidocaine concentration

| Propofol 1% | Particle size (nm)/pH | | | | |
|---|---|---|---|---|---|
| Lidocaine concentration | At reconstitution | Day 1 | Day 2 | Day 3 | Day 4 |
| 0.2% (2 mg/mL) | 35.1/6.35 | 35.8/6.4 | 36.8/6.20 | 39.2/6.36 | 39.9/6.26 |
| 1% (10 mg/mL) | 33.9/6.53 | 34.5/6.38 | 33.0/6.39 | 37.5/6.49 | 37.0/6.43 |
| 2% (20 mg/mL) | 31.9/6.87 | 34.5/6.56 | 33.2/6.60 | 32.4/6.71 | 31.1$6.65 |

Example 13

Two other liquid biologically active agents have also been successfully loaded in PVP-PLA micelles using the same procedure. 2-phenoxyethanol (50 mg/mL) and quinaldine (10 mg/mL) were added to aqueous PVP-PLA solutions (90 mg/mL) containing 75 mM (final concentration) of sodium phosphate buffer (pH 7.4). The clear solutions were then diluted to suitable concentration for UV absorbance measurements prior to freezing and lyophilization. The resulting lyophilizate was then reconstituted by addition of water to approximately the same concentration, i.e. 50 mg/mL for 2-phenoxyethanol and 10 mg/mL for quinaldine. Clear solutions were obtained. UV absorbance was then measured to assess the presence of the two drugs. Results below indicate that the two biologically active liquids were retained in the PVP-PLA, micelles.

TABLE 17

Formulation 1: 2- Phenoxyethanol (final concentration of drug = 50 mg/mL)

| Formulation 1 | Abs (228 nm) |
|---|---|
| Before freeze drying | 0.76040 |
| After reconstitution | 0.62017 |

Formulation 1. was diluted with USP water to a 0.5 mg/mL concentration for UV measurement

TABLE 18

Formulation 2: Quinaldine (final concentration of drug = 10/mL)

| Formulation 2 | Abs (225 nm) |
|---|---|
| Before freeze drying | 2.08290 |
| After reconstitution | 1.72110 |

Formulation 2 was diluted with USP water to a 0.1 mg/mL concentration for UV measurement.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and drawings/ figures.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims.

Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A solid product suitable for reconstitution to an essentially clear, stable solution upon addition of an aqueous reconstituting solution thereto, said solid product comprising a mixture of
    at least one amphiphilic copolymer of poly(N-vinylpyrrolidone)-poly(lactide),
    and
    at least one water-insoluble, biologically active agent that is liquid at room temperature loaded within said amphiphilic copolymer so that said biologically active agent is associated with said amphiphilic copolymer in a solid product free of organic solvent;
    whereby upon hydration with a reconstituting aqueous solution, said solid product forms said essentially clear, stable solution in which said at least one biologically active agent is present as stable nanodispersions or micelles loaded with said biologically active agent.

2. The solid product according to claim 1, which comprises about 0.1% to about 25% w/w of said biologically active agent.

3. The solid product according to claim 2, which comprises about 1% to about 12% w/w of said biologically active agent.

4. The solid product according to claim 1, wherein said biologically active agent is adapted for use as an intravenous injection.

5. The solid product according to claim 1, wherein said biologically active agent is an anaesthetic agent.

6. The solid product according to claim 1, wherein said liquid biologically active agent is selected from the group consisting of propofol, 2-phenoxyethanol, quinaldine, methoxyflurane, and combinations thereof.

7. The solid product according to claim 5, wherein said anaesthetic agent is propofol.

8. The solid product according to claim 1, which is obtained by lyophilizing or spray-drying a mixture of said at least one amphiphilic copolymer, said at least one biologically active agent and a solvent of water or phosphate buffer.

9. The solid product according to claim 8, wherein said solvent is water.

10. The solid product according to claim 1, wherein the amphiphilic copolymer is poly(N-vinylpyrrolidone)-b-poly(d,l-lactide) (PVP-PDLLA).

11. A process for the production of a solid product suitable for reconstitution to a clear stable solution upon addition of an aqueous solution thereto, which comprises:
(a) forming a first mixture comprising a solution of at least one amphiphilic copolymer of poly(N-vinylpyrrolidone)-polylactide, and at least one solvent selected from the group consisting of water and an aqueous solution, under conditions to achieve micelle or nanodispersion formation;
(b) adding at least one water-insoluble biologically active agent that is liquid at room temperature to said first mixture in such a manner to load said micelle or nanodispersion therewith and form a second mixture; and
(c) treating said second mixture under conditions effective to remove said solvent therefrom while forming a solid product that contains said biologically active agent associated with said amphiphilic copolymer, wherein said solid product upon hydration with a second aqueous solution forms a clear stable solution in which said biologically active agent is present as nanodispersion or as a micelle loaded with said biologically active agent.

12. The process according to claim 11, further comprising, after step (c), hydrating the solid product to produce a stabilized nanodispersion or loaded micelle.

13. The process according to claim 11, further comprising adding at least one additive to said first and/or second mixture.

14. The process according to claim 11, further comprising filtering said solution produced step (a) to yield a sterile filtrate.

15. The process according to claim 12, wherein said step of hydrating includes combining said solid product with a sufficient amount of water, saline solution or dextrose solution.

16. The process according to claim 13, wherein said additive is at least one member selected from the group consisting of a buffer, a cryoprotectant, an analgesic, a lyoprotectant, a bulk forming agent, lactose, trehalose, mannitol, saccharides, amino acids soluble in said solvent, and combinations thereof.

17. The process according to claim 11, wherein said forming step further includes at least one dissolution enhancing means selected from the group consisting of sonicating, vortexing and heating.

18. The process according to claim 11, wherein said water insoluble biologically active agent is selected from the group consisting of propofol, 2-phenoxyethanol, quinaldine, and methoxyflurane, and combinations thereof.

19. The process according to claim 11, wherein the amphiphilic copolymer is poly(N-vinylpyrrolidone)-b-poly(d,l-lactide) (PVP-PDLLA).

* * * * *